(12) United States Patent
Kim et al.

(10) Patent No.: US 9,375,503 B2
(45) Date of Patent: Jun. 28, 2016

(54) AIR CONDITIONER FOR AUTOMOBILE

(71) Applicant: HALLA CLIMATE CONTROL CORP., Daejeon (KR)

(72) Inventors: Jae Ho Kim, Daejeon (KR); Jin Hyuck Kim, Daejeon (KR); Sung Je Lee, Daejeon (KR); Yong Jun Jee, Daejeon (KR); Sang Chul Byon, Daejeon (KR); Nam Jun Lee, Daejeon (KR); Yong Sung Kwon, Daejeon (KR)

(73) Assignee: HANON SYSTEMS, Daejeon (KR)

( * ) Notice: Subject to any disclaimer, the term of this patent is extended or adjusted under 35 U.S.C. 154(b) by 0 days.

(21) Appl. No.: 14/540,181

(22) Filed: Nov. 13, 2014

(65) Prior Publication Data

US 2015/0068705 A1 Mar. 12, 2015

Related U.S. Application Data

(63) Continuation-in-part of application No. 13/604,797, filed on Sep. 6, 2012, now Pat. No. 8,887,521.

(30) Foreign Application Priority Data

| Sep. 9, 2011 | (KR) | ......................... | 10-2011-0091978 |
| Nov. 23, 2011 | (KR) | ......................... | 10-2011-0123031 |
| Nov. 23, 2011 | (KR) | ......................... | 10-2011-0123037 |
| Feb. 22, 2012 | (KR) | ......................... | 10-2012-0017787 |

(51) Int. Cl.
*F24F 3/16* (2006.01)
*A61L 9/14* (2006.01)
*B60H 3/00* (2006.01)

(52) U.S. Cl.
CPC ................ *A61L 9/14* (2013.01); *B60H 3/0021* (2013.01); *B60H 2003/0064* (2013.01); *Y10T 403/3966* (2015.01)

(58) Field of Classification Search
CPC ................ F24F 6/14; F24F 2003/1689; F24F 2003/2006; F24F 2003/14; F24F 2003/143; F24F 2003/146; F17C 13/00; F17C 17/04; F17C 2201/058; F17C 2205/0157; B60H 1/00014; B60H 2001/00192; B60H 2001/002; B60H 1/00564; B60H 3/0007; B60H 3/0021
See application file for complete search history.

(56) References Cited

U.S. PATENT DOCUMENTS 3,430,268 A * 3/1969 Zoberg ..................... E03D 9/08
4/420.1
5,257,467 A 11/1993 White
(Continued)

FOREIGN PATENT DOCUMENTS

| EP | 01195277 | 4/2002 |
| EP | 2221202 | 8/2010 |

(Continued)

OTHER PUBLICATIONS

Office Action issued on corresponding Korean Patent application No. 10-2011-0091978 dated Oct. 30, 2013.
(Continued)

*Primary Examiner* — Frantz Jules
*Assistant Examiner* — Erik Mendoza-Wilkenfe
(74) *Attorney, Agent, or Firm* — Hauptman Ham, LLP

(57) ABSTRACT

Provided is an air conditioner for an automobile capable of having uniform perfume performance in a width direction of the automobile by discharging air mixed with a perfume component supplied from a perfume generating unit through a discharging part.

9 Claims, 25 Drawing Sheets

(56) References Cited

U.S. PATENT DOCUMENTS

| | | | | |
|---|---|---|---|---|
| 5,664,423 | A | * | 9/1997 | Akazawa .......................... 62/78 |
| 5,737,937 | A | * | 4/1998 | Akazawa ................. A61L 9/12 165/95 |
| 5,768,911 | A | | 6/1998 | Dube |
| 5,911,742 | A | * | 6/1999 | Akazawa ................. A61L 9/12 165/41 |
| 6,019,288 | A | * | 2/2000 | Arold ................. B60H 1/00064 165/204 |
| 6,079,640 | A | * | 6/2000 | Merritts ................... B05B 1/20 239/532 |
| 6,578,771 | B2 | * | 6/2003 | Kaneura ............ B60H 1/00064 165/42 |
| 6,622,787 | B1 | * | 9/2003 | Toyoshima ........ B60H 1/00064 165/203 |
| 8,196,902 | B1 | * | 6/2012 | Pystin ............................ 261/26 |
| 2002/0074421 | A1 | * | 6/2002 | Choquet ................. A61L 9/12 239/58 |
| 2002/0130204 | A1 | | 9/2002 | Chao ........................ B05B 1/20 239/548 |
| 2003/0186643 | A1 | * | 10/2003 | Feuillard ................ A61L 9/122 454/157 |
| 2006/0243826 | A1 | * | 11/2006 | Bevilacqua .............. B05B 1/20 239/450 |
| 2007/0087680 | A1 | * | 4/2007 | Kim .................. B60H 1/00514 454/229 |
| 2007/0163627 | A1 | * | 7/2007 | Lim ........................ B05B 1/20 134/94.1 |
| 2010/0043470 | A1 | | 2/2010 | Kang et al. |
| 2010/0044276 | A1 | | 2/2010 | Marks et al. |
| 2011/0009044 | A1 | * | 1/2011 | Seto .................. B60H 1/00028 454/143 |

FOREIGN PATENT DOCUMENTS

| | | |
|---|---|---|
| FR | 2825949 | 12/2002 |
| FR | 2833533 | 6/2003 |
| JP | 6-32126 | 4/1994 |
| JP | 06-185673 | 7/1994 |
| JP | 2008162475 | 7/2008 |
| KR | 100901413 | 6/2009 |
| KR | 2010-0093726 | 8/2010 |
| KR | 1020100093725 | 8/2010 |

OTHER PUBLICATIONS

Office Action issued on corresponding Korean Patent application No. 10-2011-0123031 dated Dec. 20, 2013.
Notice of Allowance issued on corresponding Korean Patent application No. 10-2011-0123037 dated Dec. 20, 2013.
Office Action issued on corresponding Chinese Patent application No. 201210333016.5 dated Jun. 25, 2014.
Extended European Search Report for corresponding European Patent application No. 12006265.8 dated May 6, 2014.
Notice of Allowance issued on corresponding Korean Patent application No. 10-2011-0091978 dated May 20, 2014.
Notice of Allowance issued on corresponding Korean Patent application No. 10-2011-0123031 dated Jun. 24, 2014.

* cited by examiner

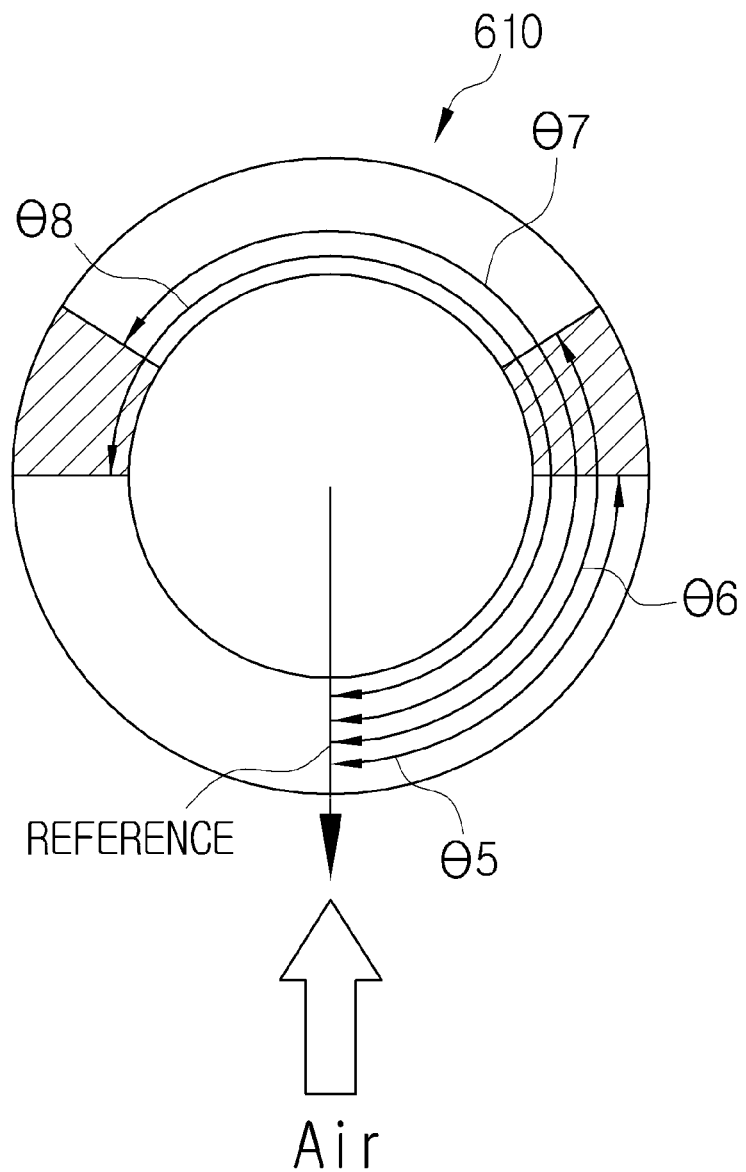

AIR CONDITIONER FOR AUTOMOBILE

CROSS-REFERENCE TO RELATED APPLICATIONS

This application claims priority under 35 U.S.C. §119 to Korean Patent Application Nos. 10-2011-0091978 filed on 9 Sep., 2011, 10-2011-0123031 filed on 23 Nov., 2011, 10-2011-0123037 filed on 23 Nov., 2011 and 10-2012-0017787 filed on 22 Feb., 2012 in the Korean Intellectual Property Office, the disclosure of which is incorporated herein by reference in its entirety.

TECHNICAL FIELD

The following disclosure relates to an air conditioner for an automobile, and more particularly, to an air conditioner for an automobile capable of having uniform perfume performance in a width direction of the automobile by discharging air mixed with a perfume component supplied from a perfume generating unit into an air conditioning case through a discharging part.

BACKGROUND

An air conditioner for an automobile is an apparatus for cooling or heating an interior of the automobile by heating or cooling air in a process of introducing external air into the interior of the automobile or circulating air of the interior of the automobile.

More specifically, the air conditioner for an automobile is configured to include an air conditioning case provided with a face vent, a defrost vent, and a floor vent each having an open degree controlled by the respective doors; a blowing unit connected to an inlet of the air conditioning case to blow external air; an evaporator and a heater core provided in the air conditioning case; and a temp-door controlling open degrees of a cool air passage and a warm air passage in the air conditioning case.

Meanwhile, a perfume generating apparatus for further improving pleasantness of a passenger in an automobile has been suggested in Japanese Utility Model Laid-Open Publication No. 1994-032126 (entitled "Perfume Generating Apparatus for Automobile"), which is shown in FIG. 1.

The perfume generating apparatus 1 for an automobile is applied to an air conditioner 2 for an automobile including a blowing duct 3 inducing the blowing air to the respective vents 12, 13, and 14 having an open degree controlled by the respective doors 12d, 13d, and 14d and being in communication with an interior of the automobile; a blowing part 4 provided in the blowing duct 3; and an evaporator 5 and a heater core 6 provided in the blowing duct 3, and is configured to include a first communication passage 18 connected to a lower portion of the blowing part 4 in the blowing duct 3; a second communication passage 19 connected to a lower portion of the heater core 6; perfume containers 15, 16, and 17 provided between the first and second communication passages 18 and 19 and having a perfume received therein; and a controlling part 25 including control valves 21, 22, 23, and 24 to control the supply of a perfume component in the perfume containers 15, 16, and 17.

The perfume generating apparatus for an automobile has an advantage in that the perfume component may be sprayed into the blowing duct, be mixed with air through the blowing part, and be then supplied to the respective vents.

However, in the perfume generating apparatus for an automobile, the second communication passage sprays the perfume component at the lower portion of the heater core, such that there is a possibility that the perfume component will move to the defrost vent or the floor vent, which may cause deterioration of perfume performance.

Further, the air conditioner for an automobile generally includes a face vent formed in a width direction of the automobile so as to discharge air to the entire driver seat and passenger seat. In this configuration, the air is discharged through a plurality of extracting parts. However, it is difficult for the perfume generating apparatus for an automobile shown in FIG. 1 to uniformly supply the perfume component to the plurality of extracting parts.

Further, in the perfume generating apparatus for an automobile described above, the second communication passage discharges the perfume component in the air conditioning case, and the discharged perfume component is mixed with the air and then discharged into the interior of the automobile. However, in the perfume generating apparatus for an automobile described above, there is a difference in perfume strength according a blowing degree and an operation state of the door. Particularly, perfume strength of the perfume component discharged through the plurality of extracting parts of the face vent is not entirely uniform.

RELATED ART DOCUMENT

Patent Document

Japanese Utility Model Laid-Open Publication No. 1994-032126 (published Apr. 26, 1994)

SUMMARY

An embodiment of the present invention is directed to providing an air conditioner for an automobile capable of having uniform perfume performance in a width direction of the automobile by discharging air mixed with a perfume component supplied from a perfume generating unit into an air conditioning case through a discharging part.

In one general aspect, an air conditioner 1000 for an automobile includes: an air conditioning case 100 provided with a face vent 110 having an open degree controlled by a first door 110d, a defrost vent 120 having an open degree controlled by a second door 120d, and a floor vent 130 having an open degree controlled by a third door 130d; a blowing part 800 connected to an inlet of the air conditioning case 100 to blow external air; an evaporator 200 and a heater core 300 provided in the air conditioning case 100; a temp-door 400 controlling open degrees of a cool air passage and a warm air passage in the air conditioning case 100; a perfume generating unit 500 including an air inlet 510 through which air is introduced, an air outlet 520 through which the air is discharged, and a perfume generating part 530 generating a perfume; and a discharging part 600 connected to the air outlet 520 of the perfume generating unit 500, formed in a width direction of the air conditioning case 100 so as to supply the air transferred through the air outlet 520 into the air conditioning case 100, and provided with one or more communication hole 620.

The discharging part may include a transferring part 610 having a pipe shape and formed to be long in a length direction, and a plurality of communication holes 620 may be formed in the length direction of the transferring part 610.

The perfume generating unit 500 may be positioned at an outer side of the air conditioning case 100, and a hollow hole 101 may be formed by hollowing a predetermined region of the air conditioning case 100, such that the discharging part 600 is inserted through the hollow hole 101.

The discharging part 600 may be further provided with a connecting part 630 connected to the other side of a supply pipe 700 connected to the air outlet 520 of the perfume generating unit 500 and a supporting part 640 formed by protruding a circumference of a region between the connecting part 630 and the transferring part 610.

The hollow hole 101 may be formed at a size at which the supporting part 640 is inserted thereinto, an inner peripheral surface of the hollow hole 101 may be provided with a convex part 102 formed by protruding a predetermined region thereof inwardly, and the supporting part 640 may be provided with a concave part 641 corresponding to the convex part 102.

The discharging part 600 may includes an extension part 650 formed at one side of the supporting part 640 in an outward direction of the air conditioning case 100 so as to contact an outer surface of the air conditioning case 100.

The extension part 650 may be provided with an indicating part 651 formed by protruding a predetermined region of an outer circumference thereof so as to guide a direction corresponding to a position of the communication hole 620 formed in the transferring part 610.

The air conditioning case 100 may include the transferring part 610 of the discharging part 600 formed integrally with an inner wall thereof.

The other side of a supply pipe 700 having one side connected to the air outlet 520 of the perfume generating unit 500 may be connected to a door axis 141 of one of the first door 110d, the second door 120d, the third door 130d, and the temp-door 400 in the air conditioning case 100, and the door axis 141 connected to the supply pipe 700 may be formed in a pipe shape in which an inner portion thereof is hollowed and be provided with one or more communication hole 620 formed by hollowing a predetermined region of an outer surface thereof to form the discharging part 600.

The air conditioning case 100 may be provided with a hollow hole 101 formed by hollowing a predetermined region thereof and a fixing part 104 connected to the supply pipe 700 so as to transfer air including a perfume component into the air conditioning case 100 through the hollow hole 101, and one end portion of the door axis 141 may be in communication with the hollow hole 101 and be rotatably provided.

The perfume generating unit 500 may be fixed to the blowing part 800.

The discharging part 600 may discharge air including a perfume component in a region in which a mixture of air passing through the cool air passage and air passing through the warm air passage moves.

The discharging part 600 may discharge air including a perfume component in a region of the face vent 110.

An end portion of the face vent 110 may be connected to a plurality of extracting parts 111, 112, 113, and 114, and the communication holes 620 may be formed to correspond to all of the plurality of extracting parts 111, 112, 113, and 114, respectively.

The communication holes 620 may be formed to correspond to the centers of the spaces of the plurality of extracting parts 111, 112, 113, and 114, respectively.

The plurality of extracting parts 111, 112, 113, and 114 may include an extracting part 112 for a driver seat, an extracting part 113 for a passenger seat, and first and second side extracting parts 111 and 114 formed at both sides of the extracting part 112 for a driver seat and the extracting part 113 for a passenger seat, respectively.

In the discharging part 600, communication holes 622 and 623 corresponding to the extracting part 112 for a driver seat and the extracting part 113 for a passenger seat may be formed to be larger than communication holes 621 and 624 corresponding to the first and second side extracting parts 111 and 114.

The discharging part 600 may be provided with a plurality of communication holes 620, and the communication holes 620 may be formed to have gradually increased hollow sizes as they become distant from the supply pipe 700.

BRIEF DESCRIPTION OF THE DRAWINGS

FIG. 17 is a cross-sectional view of a third example of a discharging part of an air conditioner for an automobile according to the exemplary embodiment of the present invention.

Figure 1:
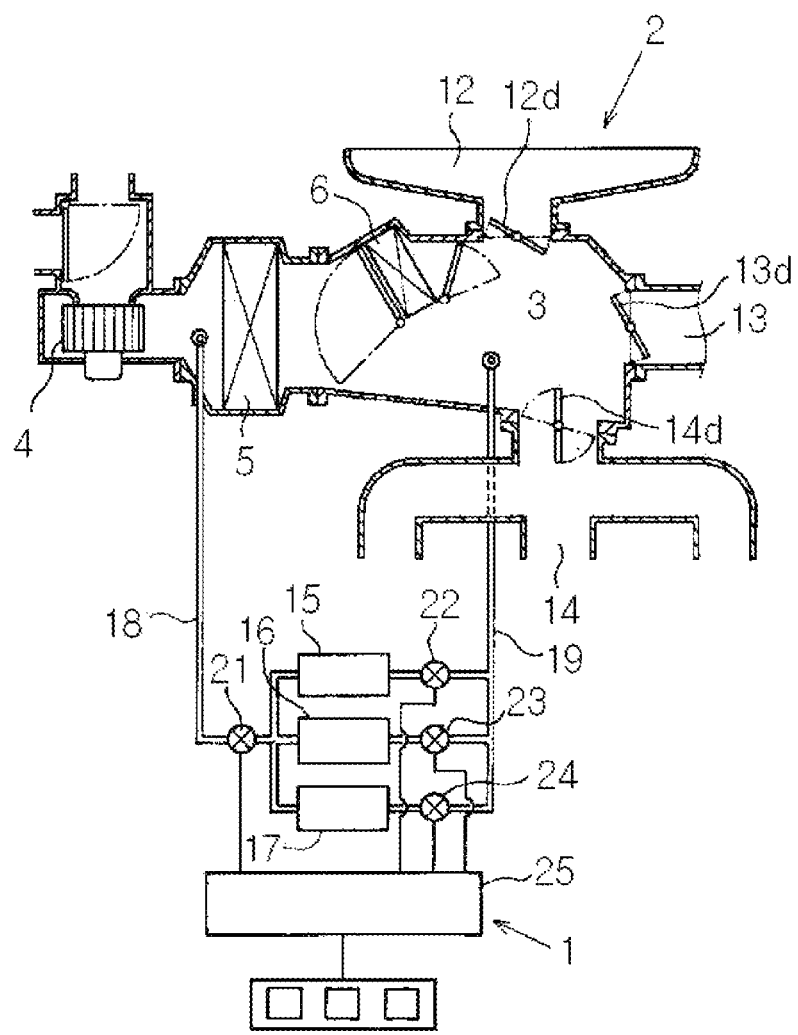
FIG. 1 is a view showing a heat exchanger according to the related art.

| [Detailed Description of Main Elements] | |
|---|---|
| 1000: Air conditioner for automobile | |
| 100: Air conditioning case | 101: Hollow hole |
| 102: Convex part | 103: Fastening groove |
| 104: Fixing part | 105: Fastening protrusion |
| 110: Face vent | 110d: Door |
| 111: First side extracting part | |
| 112: Extracting part for driver seat | |
| 113: Extracting part for passenger seat | |
| 114: Second side extracting part | |
| 120: Defrost vent | 120d: Door |
| 130: Floor vent | 130d: Door |
| 141: Door axis | 142: Step part |
| 150: Driving unit | |
| 200: Evaporator | |
| 300: Heater core | |
| 400: Temp-door | |
| 500: Perfume generating unit | 510: Air inlet |
| 520: Air outlet | |
| 530: Perfume generating part | |
| 600: Discharging part | 610: Transferring part |
| 620: Communication hole (621~624) | 630: Connecting part |
| 640: Supporting part | 641: Concave part |
| 650: Extension part | 651: Indicating part |
| 700: Supply pipe | |
| 800: Blowing part | |

DETAILED DESCRIPTION OF EMBODIMENTS

Hereinafter, an air conditioner 1000 for an automobile according to an exemplary embodiment of the present invention having the above-mentioned characteristics will be described in more detail with reference to the accompanying drawings.

The air conditioner 1000 for an automobile according to the exemplary embodiment of the present invention is configured to include an air conditioning case 100, a blowing part 800, an evaporator 200, a heater core 300, a temp-door 400, a perfume generating unit 500, and a discharging part 600.

The air conditioning case 100 corresponding to a space in which air flows is provided with a face vent 110, a defrost vent 120, and a floor vent 130 having an open degree controlled by the respective doors 110d, 120d, and 130d.

The face vent 110 corresponds to a part discharging air toward a front side (a front seat) of an interior of the automobile, the defrost vent 120 corresponds to a part discharging the air toward a window of the interior of the automobile, and the floor vent 130 corresponds to a part discharging the air toward a bottom of the front seat of the interior of the automobile, and the face vent 110, the defrost vent 120, and the floor vent 130 have the open degree controlled by the respective doors 110d, 120d, and 130d, respectively.

Figure 11:
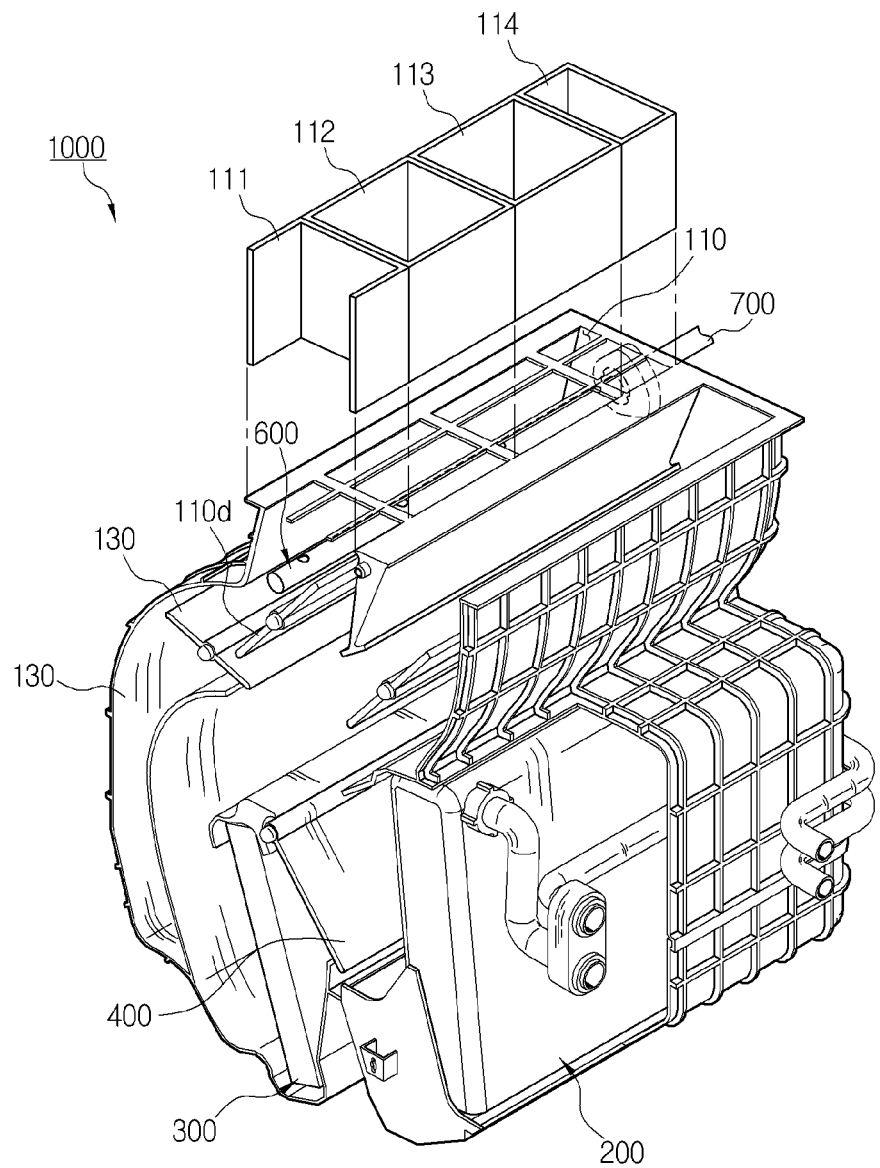
FIGS. 11 and 12 are, respectively, a perspective view and a cross-sectional view showing an air conditioner for an automobile according to another exemplary embodiment of the present invention.
Figure 12:
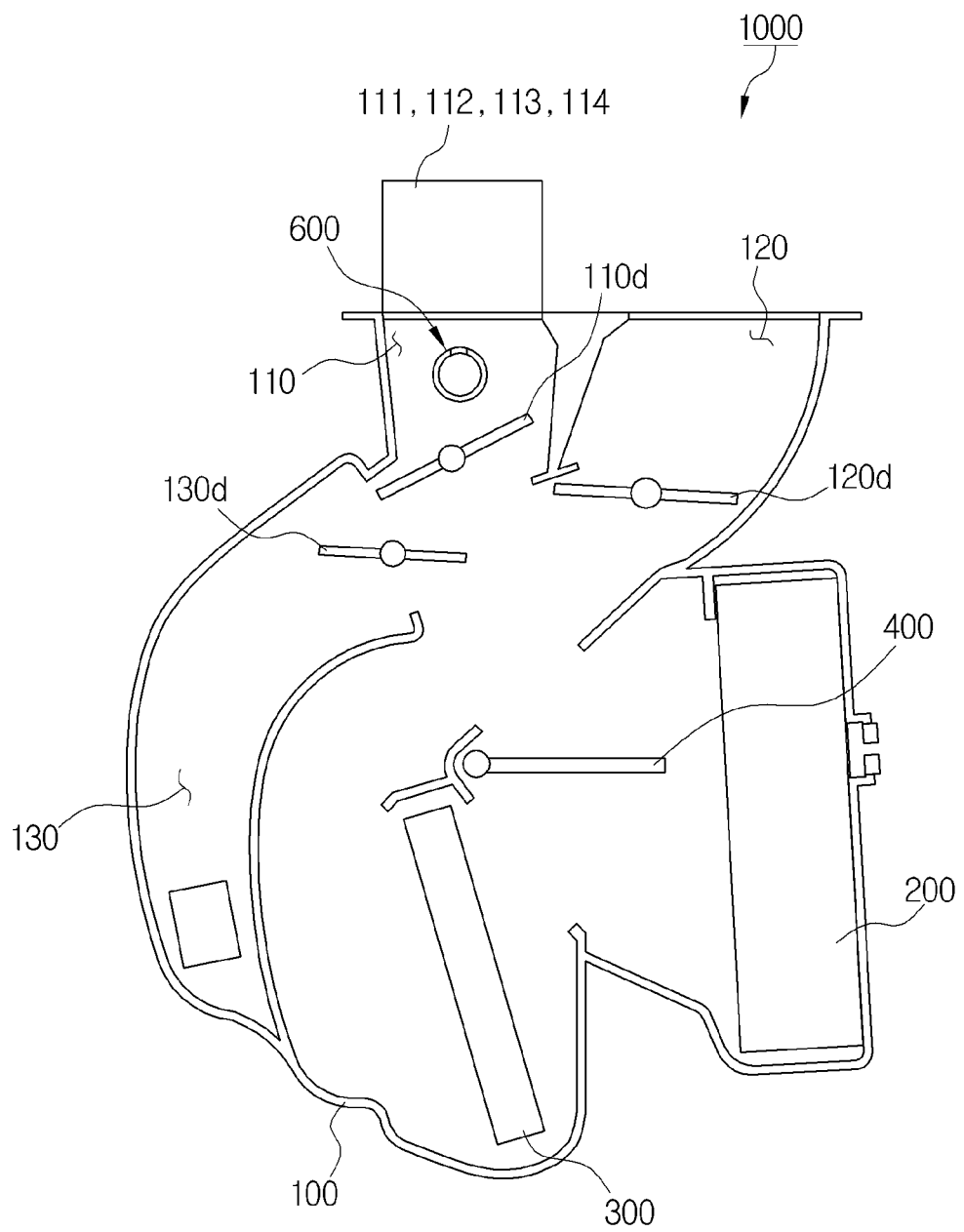

Here, the face vent 110 may be connected to a plurality of extracting parts 111, 112, 113, and 114 (See FIGS. 11 and 12).

The extracting parts 111, 112, 113, and 114 are the respective air movement passage feeding the air discharged through the face vent 110 to the front side of the automobile.

An example in which four extracting parts 111, 112, 113, and 114 are formed is shown in FIGS. 11 and 12. In this case, the extracting parts 111, 112, 113, and 114 includes an extracting part 112 for a driver seat, an extracting part 113 for a passenger seat, and first and second side extracting parts 111 and 114 formed at both sides of the extracting part 112 for a driver seat and the extracting part 113 for a passenger seat, respectively.

The air conditioning case 100 may have various forms in addition to a form shown in FIGS. 11 and 12.

The blowing part 800 is a unit provided at the air conditioning case 100 and sucking and supplying external air from an inlet that is in communication with the outside to the air conditioning case 100.

The evaporator 200 is a unit provided at a rear side of the blowing part 800 in an air flow direction by the blowing part 800 and cooling the air, and the heater core 300 is a unit provided at a rear side of the evaporator 200 in the air flow direction and heating the air.

The temp-door 400 is a unit controlling open degrees of a cool air passage and a warm air passage. When cooling is performed, the air blown by the blowing part 800 is cooled while passing through the evaporator 200, does not pass through the heater core 300 by closure of the warm air passage by the temp-door 400, and is then discharged through the vents 110, 120, and 130.

In addition, when heating is performed, the air blown by the blowing part 800 passes through the evaporator 200, is heated while passing through the heater core 300 by opening of the warm air passage by the temp-door 400, and is then discharged through the vents 110, 120, and 130.

The perfume generating unit 500 includes an air inlet 510, an air outlet 520, and a perfume generating part 530, wherein partial air is introduced into the perfume generating part 530 through the air inlet 510 and air including a perfume component is discharged through the air outlet 520.

The perfume generating unit 500 may have various configurations and is preferably positioned at an outer side of the air conditioning case 100 so as not to hinder an air flow in the air conditioning case 100.

The discharging part 600 is a unit provided in the air conditioning case 100 and discharging the air including the perfume component supplied through the air outlet 520 of the perfume generating unit 500.

The discharging part 600 may have various forms. First, an example in which the discharging part 600 includes a transferring part 610 and communication holes 620 will be described.

The transferring part 610, which is a basic component forming the discharging part 600, has a pipe shape and is formed in to be long in a length direction so that the air including the perfume component moves over the entire region in a width direction of the air conditioning case 100.

Figure 2:
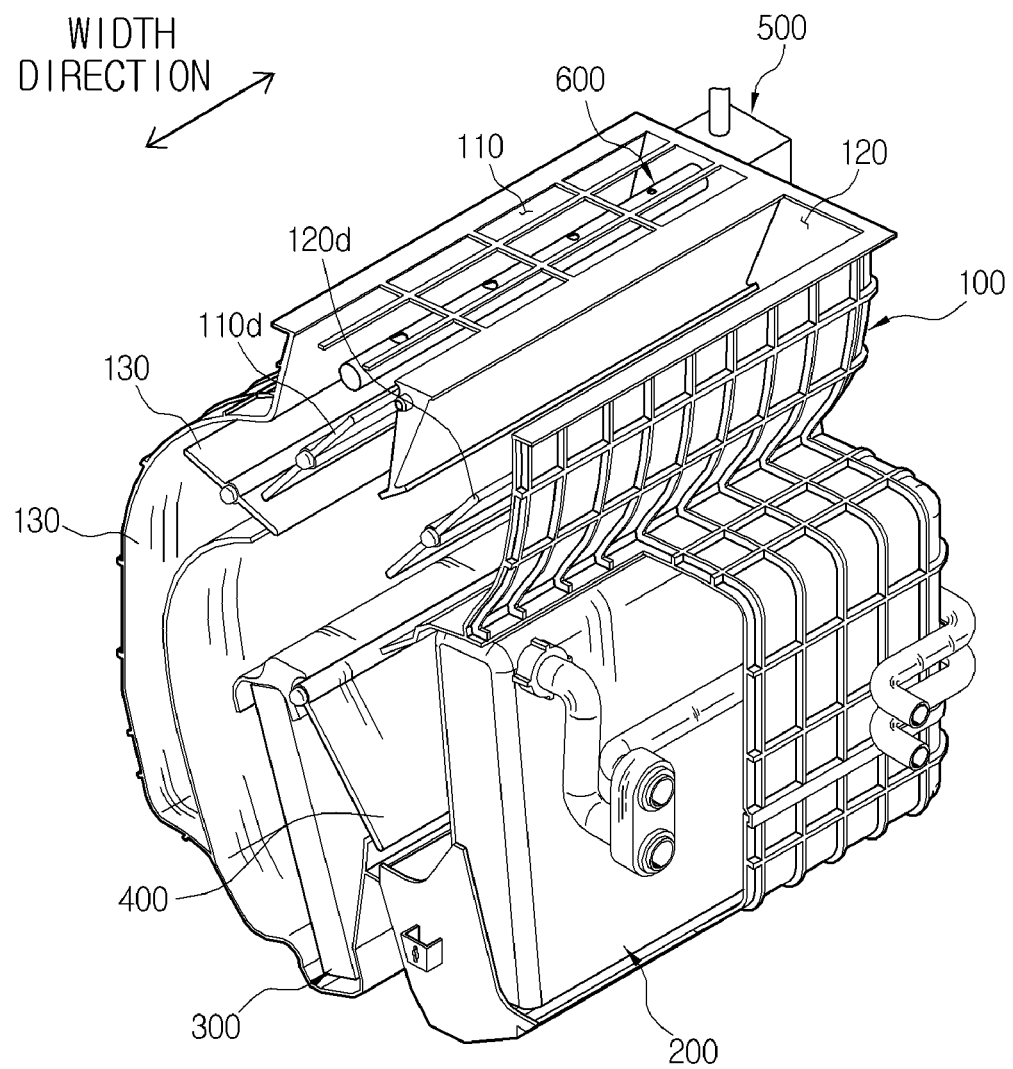
FIGS. 2 and 3 are, respectively, a perspective view and a cross-sectional view showing an air conditioner for an automobile according to an exemplary embodiment of the present invention.

In the present invention, the width direction of the air conditioning case 100 means a direction in which a length is long at a portion at which the air of the face vent 110 is discharged, which is shown in FIG. 2.

Here, the transferring part 610 has one side that is connected to the air outlet 520 of the perfume generating unit 500 and the other side that is closed.

That is, the air including the perfume component introduced into the transferring part 610 is discharged only through the communication holes 620.

Figure 6:
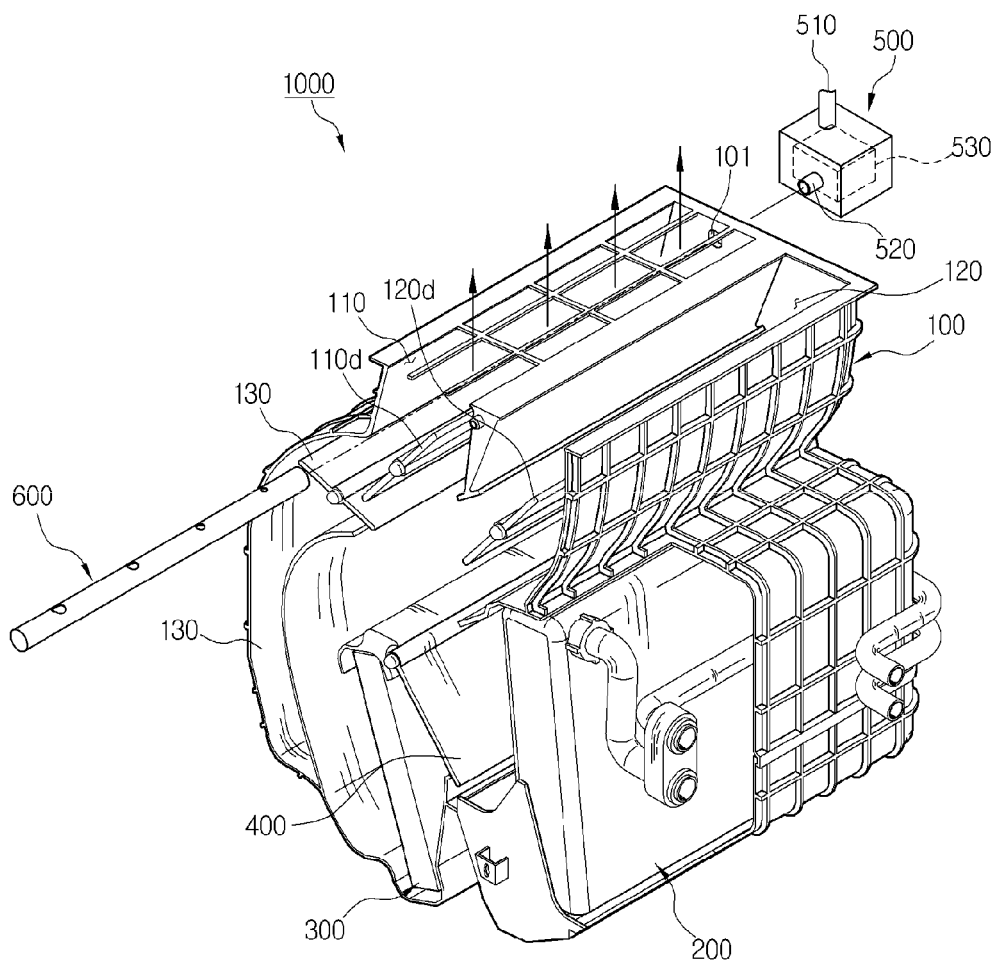
FIG. 6 is an exploded perspective view showing an air conditioner for an automobile according to another exemplary embodiment of the present invention.
Figure 7:
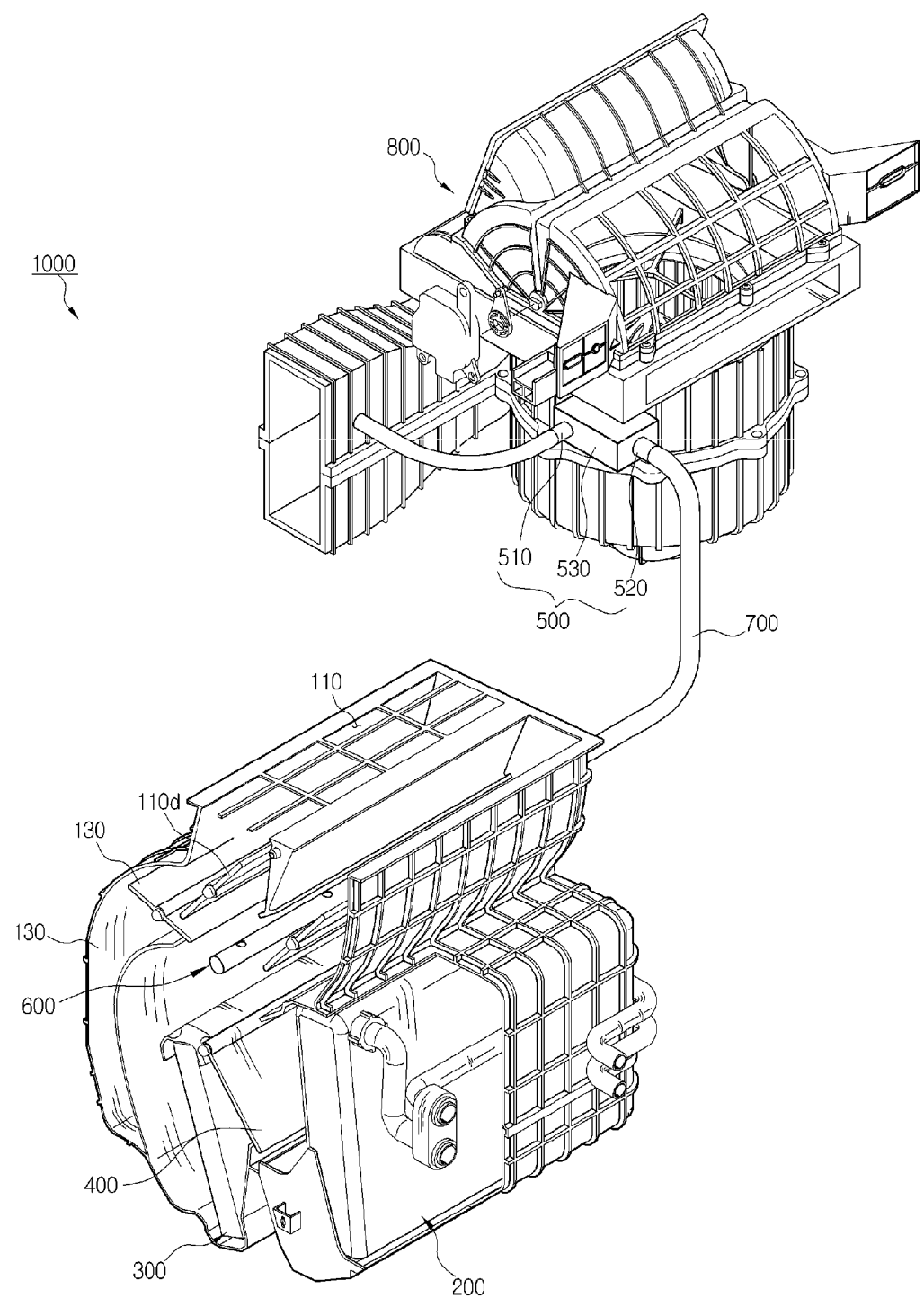
FIG. 7 is a perspective view showing an air conditioner for an automobile according to still another exemplary embodiment of the present invention.

The transferring part 610 of the discharging part 600 may be directly connected to the air outlet 520 of the perfume generating unit 500, as shown in FIG. 6, or be connected to the air outlet 520 of the perfume generating unit 500 through a supply pipe 700, as shown in FIG. 7.

As shown in FIG. 6, in the case in which the air outlet 520 of the perfume generating unit 500 is directly connected to the transferring part 610, the perfume generating unit 500 needs to be formed so that the air outlet 520 is positioned at an outer side of the air conditioning case 100.

The communication holes 620, which are formed by hollowing a predetermined region in a length direction of the transferring part 610, are formed in plural, thereby supplying the air including the perfume component into the air conditioning case 100 through the communication hole 620.

The discharging part 600 may have various forms, fixing schemes, and fixing positions. Hereinafter, each example will be described with reference to the accompanying drawings.

Figure 3:
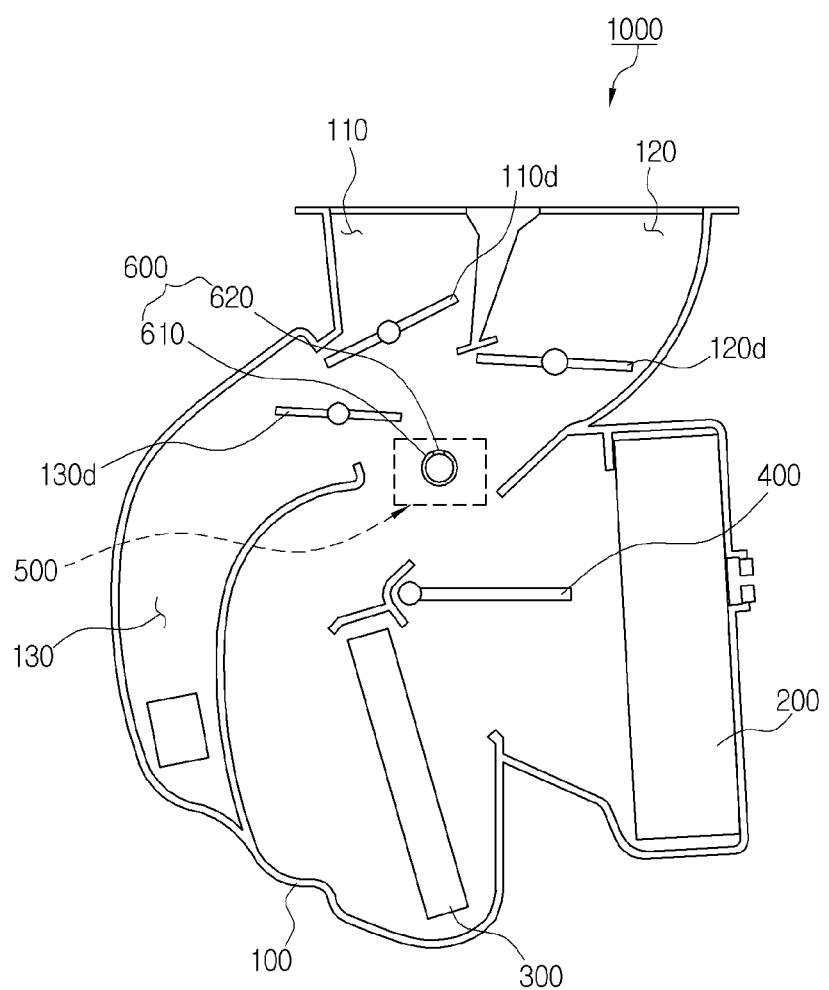

FIGS. 2 and 3 show an example in which the discharging part 600 has a pipe shape, is formed to be long in the length direction, and is provided in a downstream side region of an air flow direction of the evaporator 200 and the heater core 300. Particularly, the discharging part 600 may be provided in a region in which a mixture of air passing through the cool air passage and air passing through the warm air passage moves.

The reason is that in the case in which the discharging part 600 is provided at an upstream side of the air flow direction of the evaporator 200 and the heater core 300, perfume performance may be weakened while the perfume component passes through the evaporator 200 and the heater core 300, and the perfume component may adhere to the evaporator 200 and the heater core 300 to cause an unintended smell.

As shown in FIGS. 2 and 3, in the case in which the discharging part 600 is positioned at the region in which the mixture of the air passing through the cool air passage and the air passing through the warm air passage moves, the perfume component discharged through the discharging part 600 is mixed with the air passing through the air conditioning case 100 and is then supplied through one or more of the face vent 110, the defrost vent 120, and the floor vent 130, thereby making it possible to supply uniform perfume to the interior of the automobile.

Here, the face vent 110, the defrost vent 120, and the floor vent 130 are opened or closed by the respective doors 110d, 120d, and 130d and the passenger determines a mode in which a flow of the air supplied through the respective vents 110, 120, and 130 is determined, thereby determining the vents 110, 120, and 130 to which the air is supplied to the interior of the automobile.

The mode, which whether or not the respective vents 110, 120, and 130 are opened or closed is determined, may include a vent mode, a bi-level mode, a floor mode, a mix mode, and a defrost mode.

In other words, the air conditioner 1000 for an automobile according to the exemplary embodiment of the present invention shown in FIGS. 2 and 3 may supply the perfume component to the interior of the automobile through one or more of the face vent 110, the defrost vent 120, and the floor vent 130 regardless of a mode set by a user.

Figure 4:
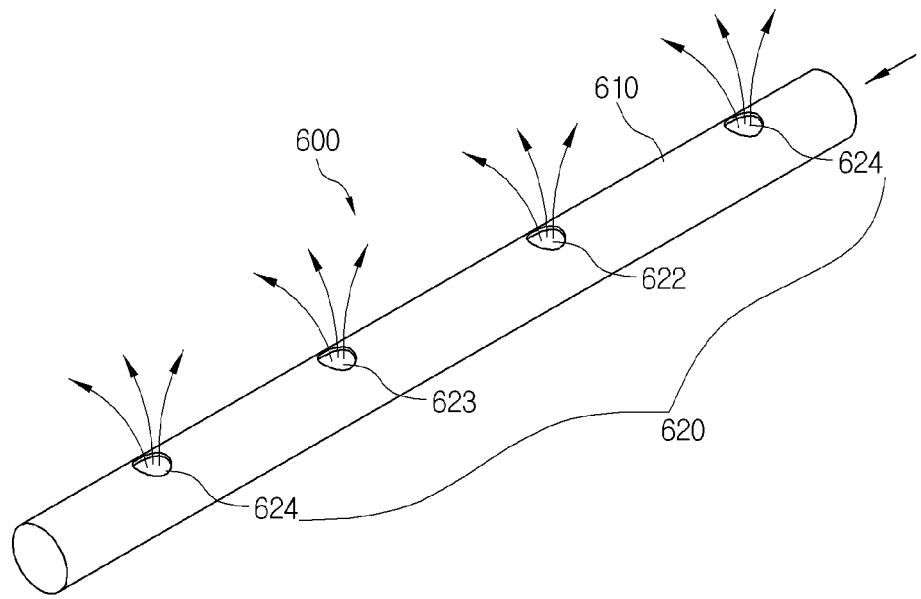
FIGS. 4 and 5 are perspective views showing a discharging part of an air conditioner for an automobile according to the exemplary embodiment of the present invention.
Figure 5:
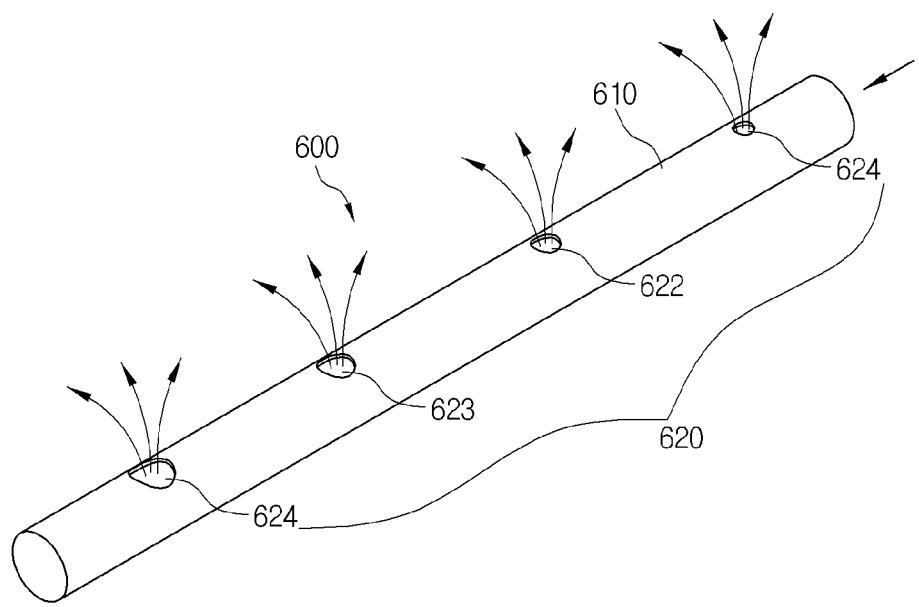

FIGS. 4 and 5 are perspective views showing an example of the discharging part 600. In FIG. 4, an example in which communication holes 620 having the same size are formed in the transferring part 610 is shown.

In FIG. 5, an example in which the communication holes 620 are formed to have gradually increased hollow sizes as they become distant from the air outlet 520 is shown.

More specifically, the air including the perfume component transferred from the air outlet 520 is introduced into the transferring part 610, moves in the transferring part 610, and is then discharged through the communication hole 620 adjacent to the air outlet 520, such that internal resistance and an air flow rate of the discharging part 600 may be reduced.

In the air conditioner 1000 for an automobile according to the exemplary embodiment of the present invention, in order to prevent a flow rate difference and a difference between amounts of air discharged through the plurality of communication holes 620 from being generated as the air including the perfume component transferred from the air outlet 520 moves in the length direction of the transferring part 610, the communication hole 620 adjacent to the air outlet 520 may be formed to have a small size and the communication holes 620 may be formed to have gradually increased sizes as they become distant from the air outlet 520 in the length direction of the transferring part 610.

In FIG. 4, the communication hole 620 most adjacent to the air outlet 520 among the communication holes 620 is denoted by a reference numeral 621, and remaining communication holes 620 are sequentially denoted by 622, 623, and 624 in the length direction of the transferring part 610.

FIG. 6, which is an exploded perspective view showing another example of the air conditioner 1000 for an automobile according to the exemplary embodiment of the present invention, shows an example in which a hollow hole 101 is formed by hollowing a predetermined region of the air conditioning case 100, such that the discharging part 600 is inserted through the hollow hole 101, and the discharging part 600 is directly connected to the air outlet 520 of the perfume generating unit 500.

Here, in the air conditioner 1000 for an automobile according to the exemplary embodiment of the present invention, a sealing member for preventing the air in the air conditioning case 100 from being leaked through the hollow hole 101 or a unit for fixing the discharging part 600 to the air conditioning case 100 may be used.

In addition, the discharging part 600 may be positioned at a region of the face vent 110 in the region in which the mixture of the air passing through the cool air passage and the air passing through the warm air passage moves.

In the case in which the discharging part 600 is positioned at the region of the face vent 110, the perfume component is not supplied in all of the modes; however, the perfume component having high concentration may be supplied to the front seat side.

Since the passenger is necessarily positioned on the driver seat of the front seat in all of the automobiles, according to the example shown in FIG. 6, the perfume may be effectively supplied to the passenger of the front seat.

FIG. 7, which is a perspective view showing another example of the air conditioner 1000 for an automobile according to the exemplary embodiment of the present invention, is similar to FIG. 6 and shows an example in which the discharging part 600 and the perfume generating unit 500 are connected to each other through the supply pipe 700.

Here, the perfume generating unit 500 is fixed to the blowing part 800, such that when the blowing part 800 is operated, the perfume generating part 530 is opened, thereby making it possible to allow the perfume component to be included in the air.

Figure 8:
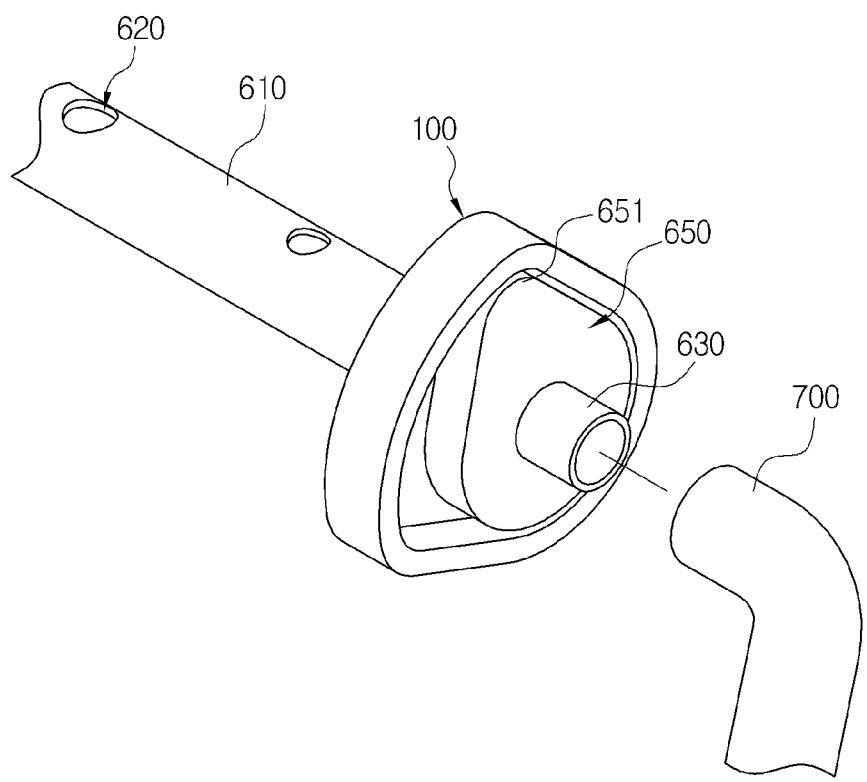
FIGS. 8 to 10 are, respectively, a partial perspective view, an exploded perspective view, and a cross-sectional view showing a connection state of the air conditioner for an automobile shown in FIG. 7.
Figure 9:
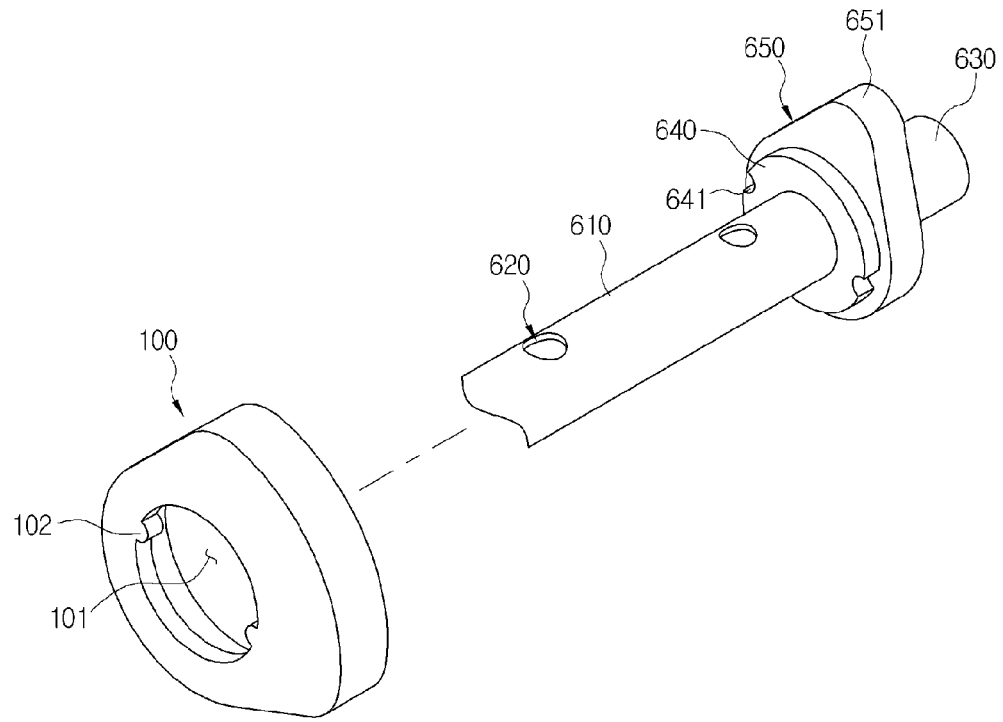
Figure 10:
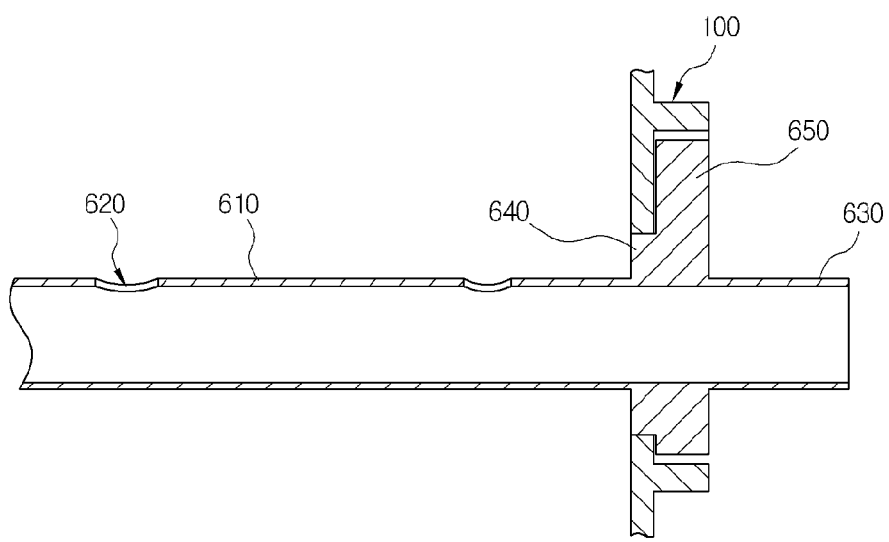

In addition, the discharging part 600 may be configured to include a connecting part 630 and a supporting part 640. A specific example of the discharging part 600 is shown in FIGS. 8 to 10.

The connecting part 630, which is a component formed at an end portion of the transferring part 610, is connected to the other side of the supply pipe 700 connected to the air outlet 520 of the perfume generating unit 500.

The supporting part 640 is a region formed by protruding a circumference of a region between the connecting part 630 and the transferring part 610.

Here, the hollow hole 101 may be formed at a size at which the transferring part 610 may be inserted thereinto.

Further, in the air conditioner 1000 for an automobile according to the exemplary embodiment of the present invention, as shown in FIGS. 8 and 9, the hollow hole 101 may be formed at a size at which the supporting part 640 may be inserted thereinto, an inner peripheral surface of the hollow hole 101 may be provided with a convex part 102, and the supporting part 640 may be provided with a concave part 641.

The example shown in FIGS. 8 and 9 may make a position at which the discharging part 600 is fixed to the air conditioning case 100 clear.

Further, in the air conditioner 1000 for an automobile according to the exemplary embodiment of the present invention, one side of the supporting part 640 in an outward direction of the air conditioning case 100 may be further provided with an extension part 650 extended to contact an outer surface of the air conditioning case 100.

In other words, the extension part 650, which is a component protruding outwardly so as to be stepped with respect to the supporting part 640, is formed to contact the outer surface of the air conditioning case 100.

In the case in which the extension part 650 is not formed, it is preferable that the concave part 641 of the discharging part 600 is formed at one side of the supporting part 640 in the outward direction of the air conditioning case 100 so as to correspond to the convex part 102 and is formed only at a predetermined region in a height at which the entire supporting part 640 is formed to allow a depth at which the entire discharging part 600 is locked to and inserted into the air conditioning case 100 to be controlled.

In FIGS. 8 and 9, only a configuration in a predetermined region of the air conditioning case 100 in which the hollow hole 101 and the convex part 102 are formed is shown.

In addition, although not denoted by a reference numeral, a guide may protrude on the outer surface of the air conditioning case 100 in order to guide a position of the extension part 650 of the discharging part 600 to limit a rotatable region and further facilitate an assembling process of the discharging part 600 (See FIG. 9).

The convex part 102 and the concave part 641 may have various numbers and angles.

In the air conditioner 1000 for an automobile according to the exemplary embodiment of the present invention, the convex part 102 and the concave part 641 are formed, such that the discharging part 600 may be fixed at a specific position so as to supply the air including the perfume component at the specific position without being rotated and may be maintained in a state in which it is firmly fixed.

In addition, in the air conditioner 1000 for an automobile according to the exemplary embodiment of the present invention, the extension part 650 is formed, thereby making it possible to reduce the possibility that the air in the air conditioning case 100 will be leaked to the outside.

Further, the extension part 650 may be provided with an indicating part 651 formed by protruding a predetermined region of an outer circumference so as to guide a direction corresponding to a position of the communication hole 620 formed in the transferring part 610.

In FIG. 8, an example in which the extension part 650 has a circular shape and has a predetermined region protruding in one direction, such that it has an approximate water drop shaped cross section is shown. However, in the air conditioner 1000 for an automobile according to the exemplary embodiment of the present invention, the indicating part 651 may have various shapes as long as it may be formed by protruding the predetermined region of the outer circumference of the extension part 650 to guide a position at which the communication hole 620 is formed.

The indicating part 651 is a component for confirming the position of the communication hole 620 in a state in which the discharging part 600 and the air conditioning case 100 are assembled to each other since the air conditioning case 100 is made of an opaque material.

The air conditioner 1000 for an automobile according to the exemplary embodiment of the present invention has advantages in that an assembling process may become easy through the indicating part 651 and the guide formed on the outer surface of the air conditioning case 100 and the air including the perfume component may be supplied through the communication hole 620 at the specific position.

Figure 13:
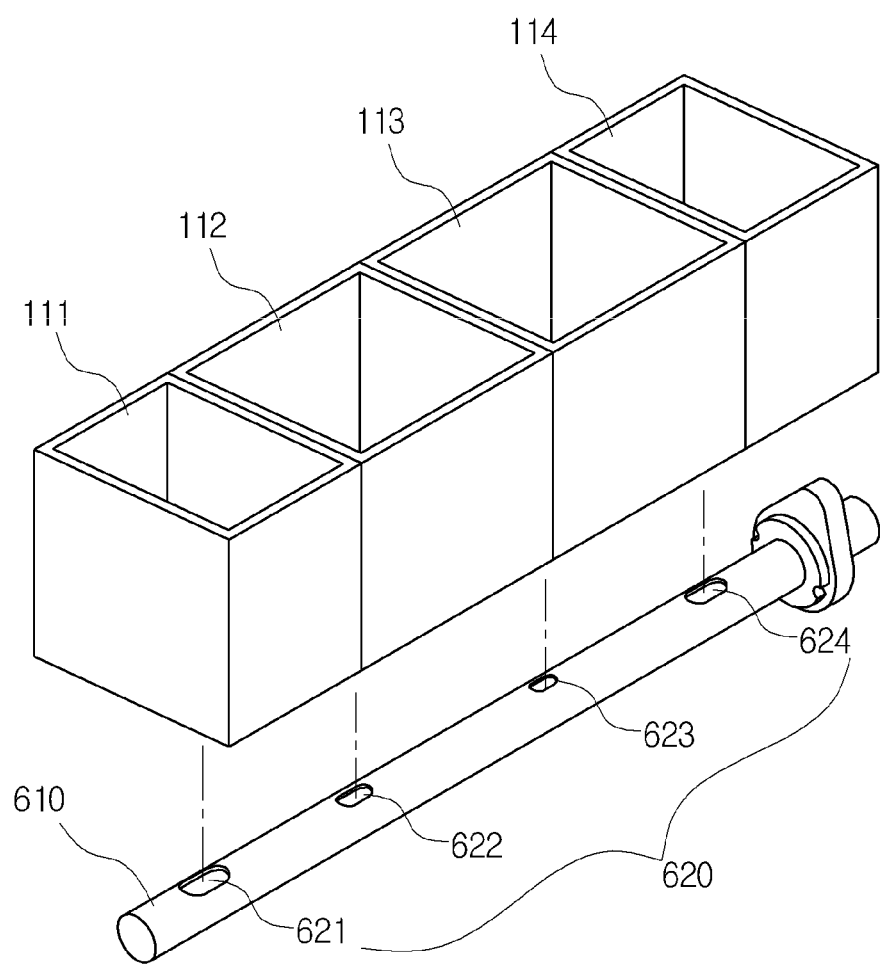
FIG. 13 is a view showing an example of a discharging part of an air conditioner for an automobile according to the exemplary embodiment of the present invention.

FIGS. 11 to 13, which are views showing still another example of the air conditioner 1000 for an automobile according to the exemplary embodiment of the present invention, are similar to the form shown in FIG. 7 and show an example in which the discharging part 600 is provided in a region at which the face vent 110 is formed.

Here, an end portion of the face vent 110 is connected to the plurality of extracting parts 111, 112, 113, and 114 positioned in the width direction of the automobile so as to uniformly discharge the air in the width direction of the automobile.

Further, the discharging part 600 may be formed so that the communication holes 620 correspond to all of the plurality of extracting parts 111, 112, 113, and 114 in order to uniformly discharge the perfume component in the air discharged through the plurality of extracting parts 111, 112, 113, and 114.

In addition, it is preferable that the communication holes 620 are positioned to correspond to the centers of the spaces of the plurality of extracting parts 111, 112, 113, and 114, respectively.

Therefore, the air conditioner 1000 for an automobile according to the exemplary embodiment of the present invention may discharge the air including the perfume component to the face vent 110 and make an amount of perfume (the air including the perfume component) discharged through the plurality of communication holes 620 corresponding to the plurality of extracting parts 111, 112, 113, and 114 connected to the face vent 110 constant. Accordingly, pleasantness of a passenger in an automobile may be improved.

The plurality of extracting parts 111, 112, 113, and 114 may include a driver seat side extracting part 111, a driver seat center extracting part 112, a passenger seat center extracting part 113, and a passenger seat side extracting part 114.

Therefore, the communication holes 620 formed in the discharging part 600 may also include a first communication hole 621 corresponding to the driver seat side extracting part 111, a second communication hole 622 corresponding to the driver seat center extracting part 112, a third communication hole 623 corresponding to the passenger seat center extracting part 113, and a fourth communication hole 624 corresponding to the passenger seat side extracting part 114.

The driver seat side extracting part 111 is in communication with a driver seat side channel for discharging the air blown within the air conditioning case 100 to a driver seat side. The driver seat side channel has an inlet stage that is in communication with the driver seat side extracting part 111 and an outlet stage that is formed at the driver seat side of the automobile so as to be opened.

The driver seat center extracting part 112 is in communication with a driver seat center channel for discharging the air blown within the air conditioning case 100 to a driver seat center. The driver seat center channel has an inlet stage that is in communication with the driver seat center extracting part 112 and an outlet stage that is formed at the driver seat center of the automobile so as to be opened.

The passenger seat center extracting part 113 is in communication with a passenger seat center channel for discharging the air blown within the air conditioning case 100 to a passenger seat center. The passenger seat center channel has an inlet stage that is in communication with the passenger seat center extracting part 113 and an outlet stage that is formed at the passenger seat center of the automobile so as to be opened.

The passenger seat side extracting part 114 is in communication with a passenger seat side channel for discharging the air blown within the air conditioning case 100 to a passenger seat side. The passenger seat side channel has an inlet stage that is in communication with the passenger seat side extracting part 114 and an outlet stage that is formed at the passenger seat side of the automobile so as to be opened.

Here, the driver seat side channel and the passenger seat side channel may be formed so as to have lengths relatively longer than those of the driver seat center channel and the passenger seat center channel. Therefore, in the case in which the same amount of perfume component is discharged to the plurality of extracting parts 111, 112, 113, and 114, perfume efficiency of the air discharged from the driver seat side channel and the passenger seat side channel may be deteriorated.

Figure 14:
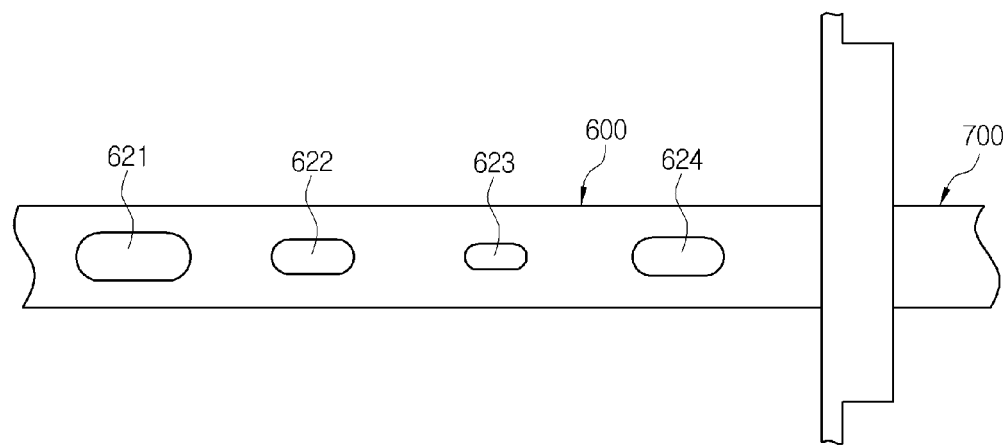
FIG. 14 is a plan view of a discharging part according to the exemplary embodiment of the present invention shown in FIG. 13.

Therefore, as shown in FIG. 14, in the air conditioner 1000 for an automobile according to the exemplary embodiment of the present invention, the second and third communication holes 622 and 623 of the communication holes 620 formed in the discharging part 600 are formed so as to have sizes smaller than those of the first and fourth communication holes 621 and 624. This is to allow a relatively larger amount of perfume component to be discharged through the first and fourth communication holes 621 and 624. Therefore, the air conditioner 1000 for an automobile according to the exemplary embodiment of the present invention has been configured so that perfume efficiency of the driver seat side extracting part 111 and the passenger seat side extracting part 114 is similar to that of the driver seat center extracting part 112 and the passenger seat center extracting part 113.

In addition, in the air conditioner 1000 for an automobile, one of the second and third communication holes 622 and 623, which is more distant from the supply pipe 700, may be formed so as to have a size larger than that of the other and one of the first and fourth communication holes 621 and 624, which is more distant from the supply pipe 700, may be formed so as to have a size larger than that of the other, in order to prevent a flow rate difference from being generated in the air transferred from the air outlet 520 and including the perfume component while the air moves in the length direction of the transferring part 610 and prevent a difference from being generated in an amount of perfume component discharged through the plurality of communication holes 620.

Therefore, the first to fourth communication holes 621 to 624 may be formed so as to have different sizes, respectively.

Figure 15:
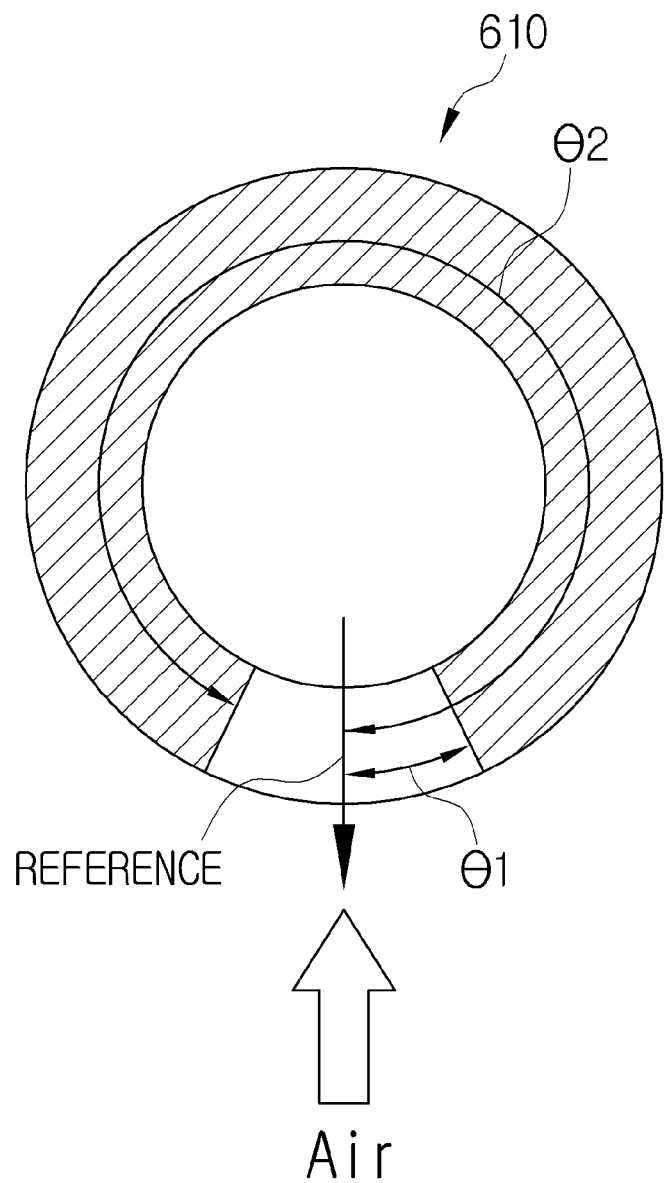
FIG. 15 is a cross-sectional view of a first example of a discharging part of an air conditioner for an automobile according to the exemplary embodiment of the present invention.

Referring to FIG. 15, when a gradient of a reference direction opposing the air flow direction from the center of the transferring part 610 of the discharging part 600 in a radial direction is defined as 0 degree, the communication holes 620 formed in the discharging part 600 may be formed at an angle between 30 and 330 degrees from the reference direction. The reason is that in the case in which the communication holes 620 are formed at an angle between 0 and 30 degrees and an angle between 330 and 360 degrees from the reference direction, discharge of the perfume component is hindered by flow pressure of the air.

Figure 16:
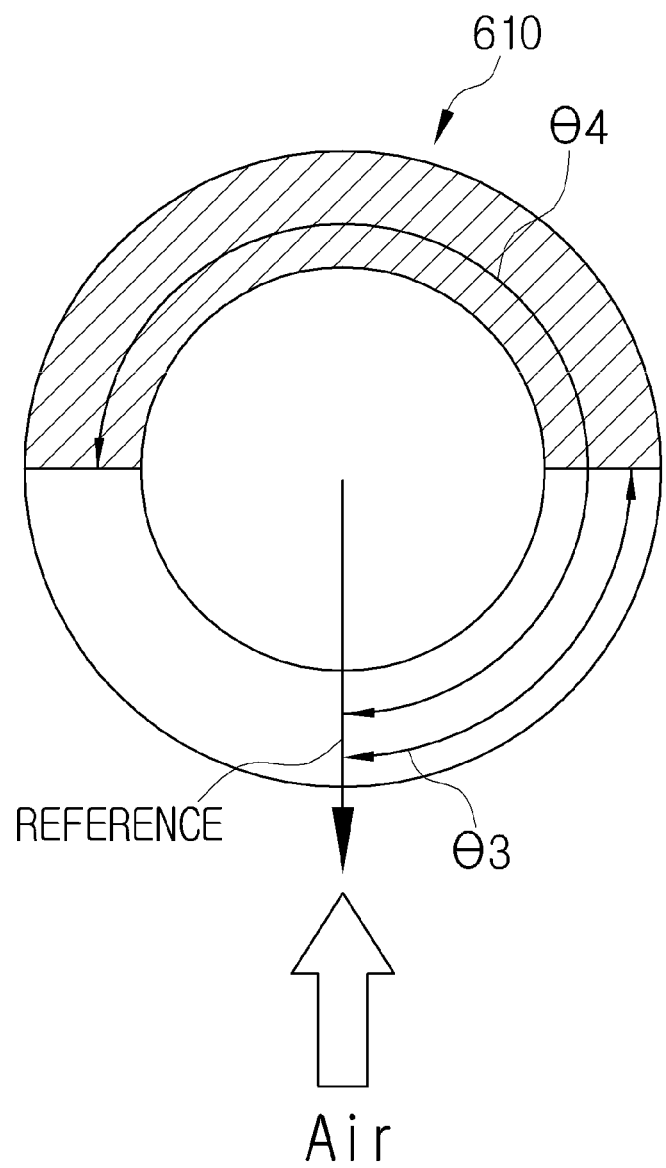
FIG. 16 is a cross-sectional view of a second example of a discharging part of an air conditioner for an automobile according to the exemplary embodiment of the present invention.

Referring to FIG. 16, more preferably, in the case in which the communication holes 620 are formed at an angle between 90 and 270 degrees from the reference direction, discharge efficiency of the perfume component may be maximized.

Referring to FIG. 17, particularly, in the case in which the communication holes 620 are formed at an angle between 90 and 135 degrees and an angle between 225 and 270 degrees from the reference direction, pressure difference between inner and outer portions of the discharging part 600 is generated by the flow pressure of the air, thereby making it possible to discharge the perfume component without a separate discharging unit and discharge a perfume in a predetermined ratio depending on a flow amount of air.

Figure 18A:
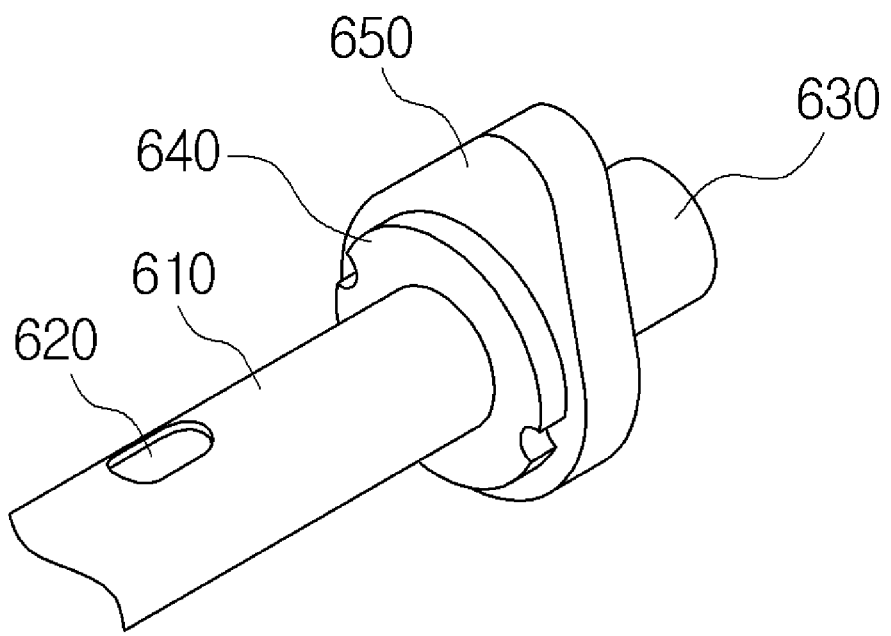
FIGS. 18A to 18D are views showing other examples of a discharging part of an air conditioner for an automobile according to the exemplary embodiment of the present invention.
Figure 18B:
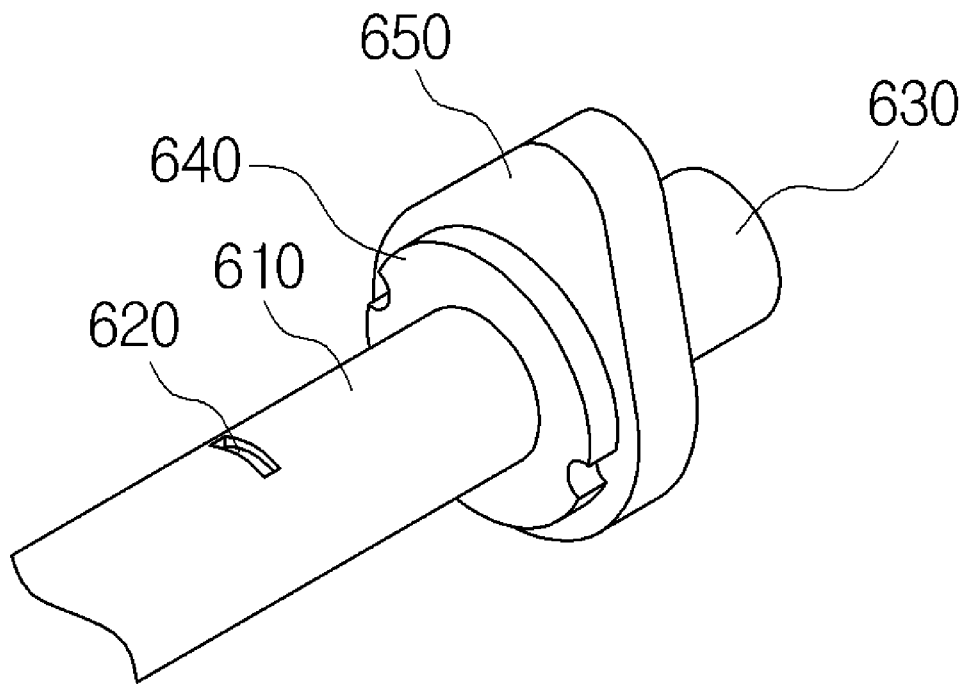
Figure 18C:
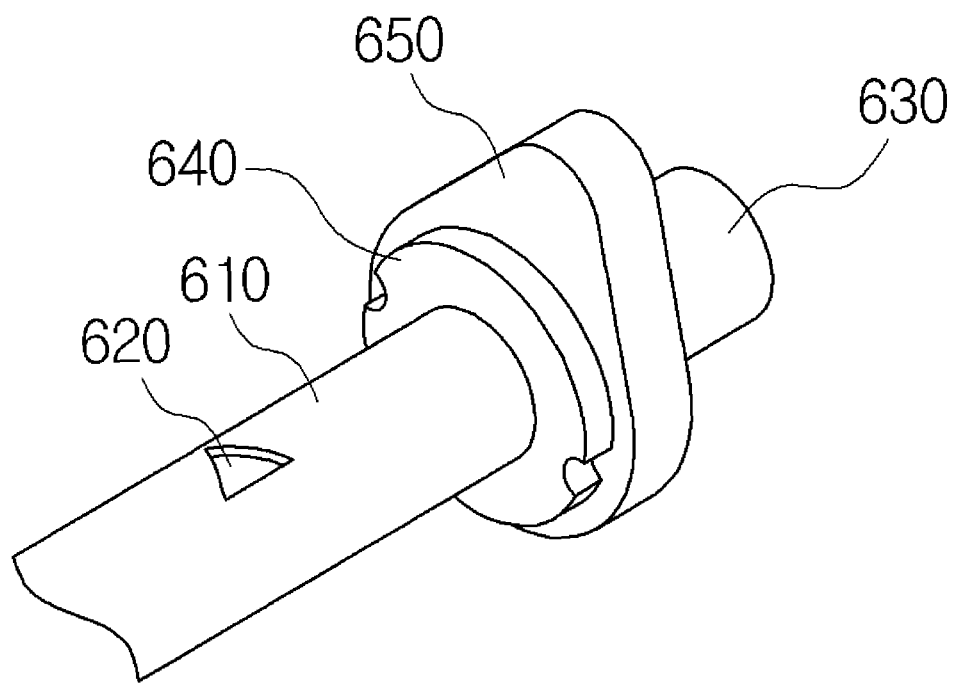
Figure 18D:
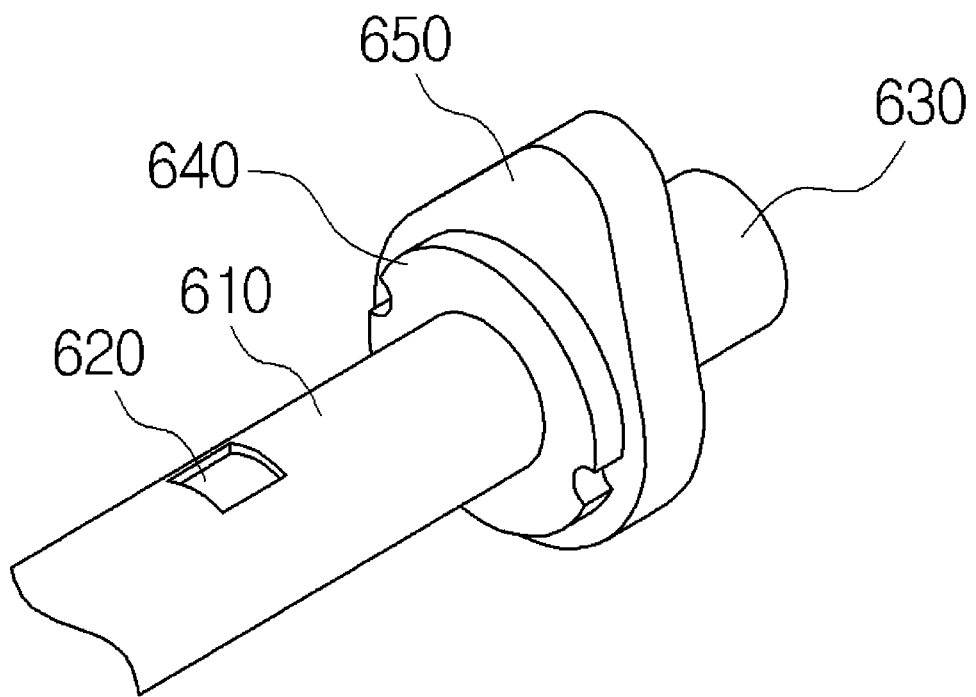

FIGS. 18A to 18D are views showing various shapes of a communication hole 620, wherein FIG. 18A shows an example of an oval communication hole 620, FIGS. 18B and 18D show an example of an approximate rectangular communication hole 620, and FIG. 18C shows an example of a triangular communication hole 620.

In the air conditioner 1000 for an automobile according to the exemplary embodiment of the present invention, the communication hole 620 may be formed to have various shapes, sizes, and numbers, in addition to the shape shown in FIGS. 18A to 18D.

FIGS. 19 to 22, which are views showing still another example of the air conditioner 1000 for an automobile according to the exemplary embodiment of the present invention, show an example in which the transferring part 610 of the discharging part 600 is formed integrally with the air conditioning case 100.

That is, the discharging part 600 is formed integrally with the air conditioning case 100 rather than being separately manufactured and then inserted into the air conditioning case 100.

In the air conditioner 1000 for an automobile according to the exemplary embodiment of the present invention, the discharging part 600 is formed integrally with the air conditioning case 100. More specifically, it is preferable that the discharging part 600 is formed integrally with an inner wall surface of the air conditioning case 100 forming the face vent 110 in order to easily manufacture the air conditioning case 100.

Figure 19:
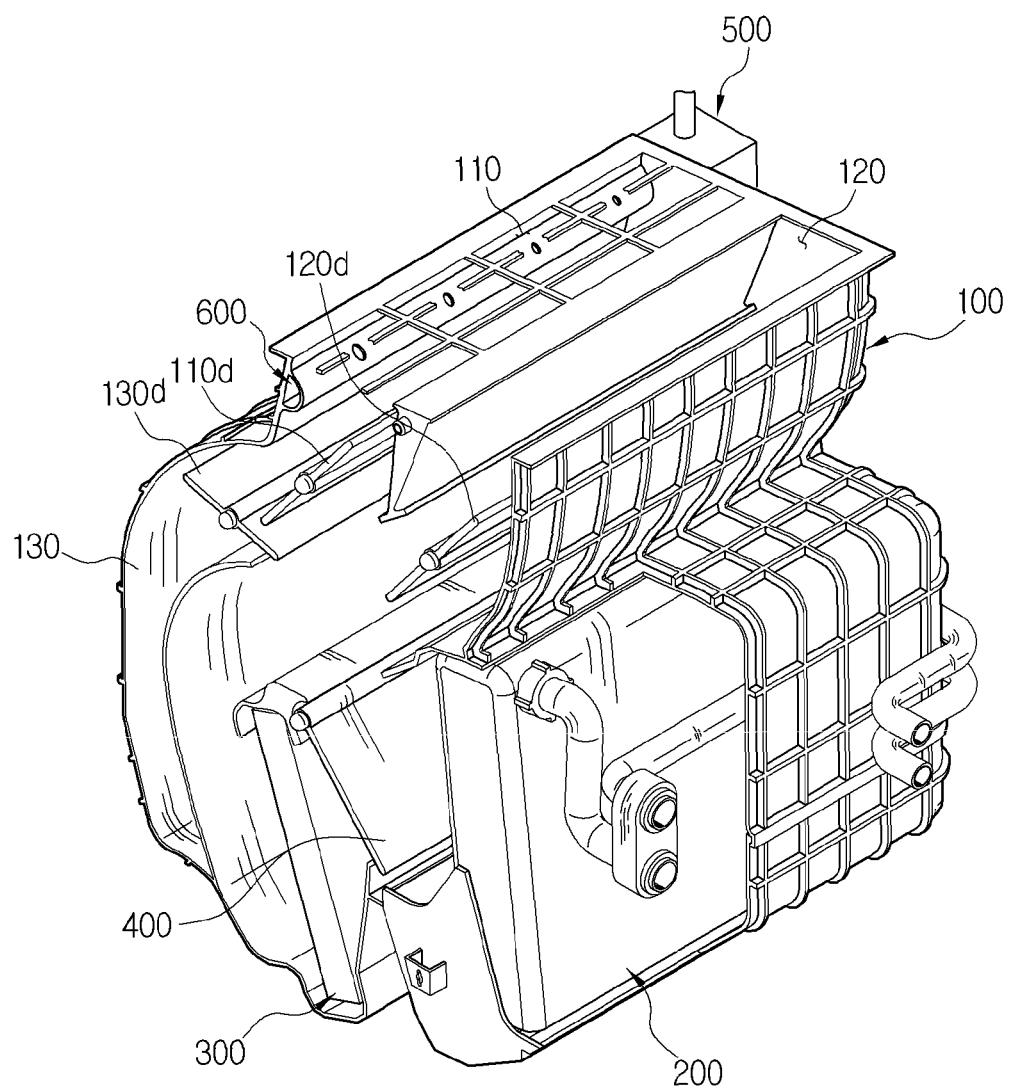
FIGS. 19 to 21 are, respectively, a perspective view, a cross-sectional view, and a partially enlarged perspective view showing an air conditioner for an automobile according to the exemplary embodiment of the present invention.
Figure 20:
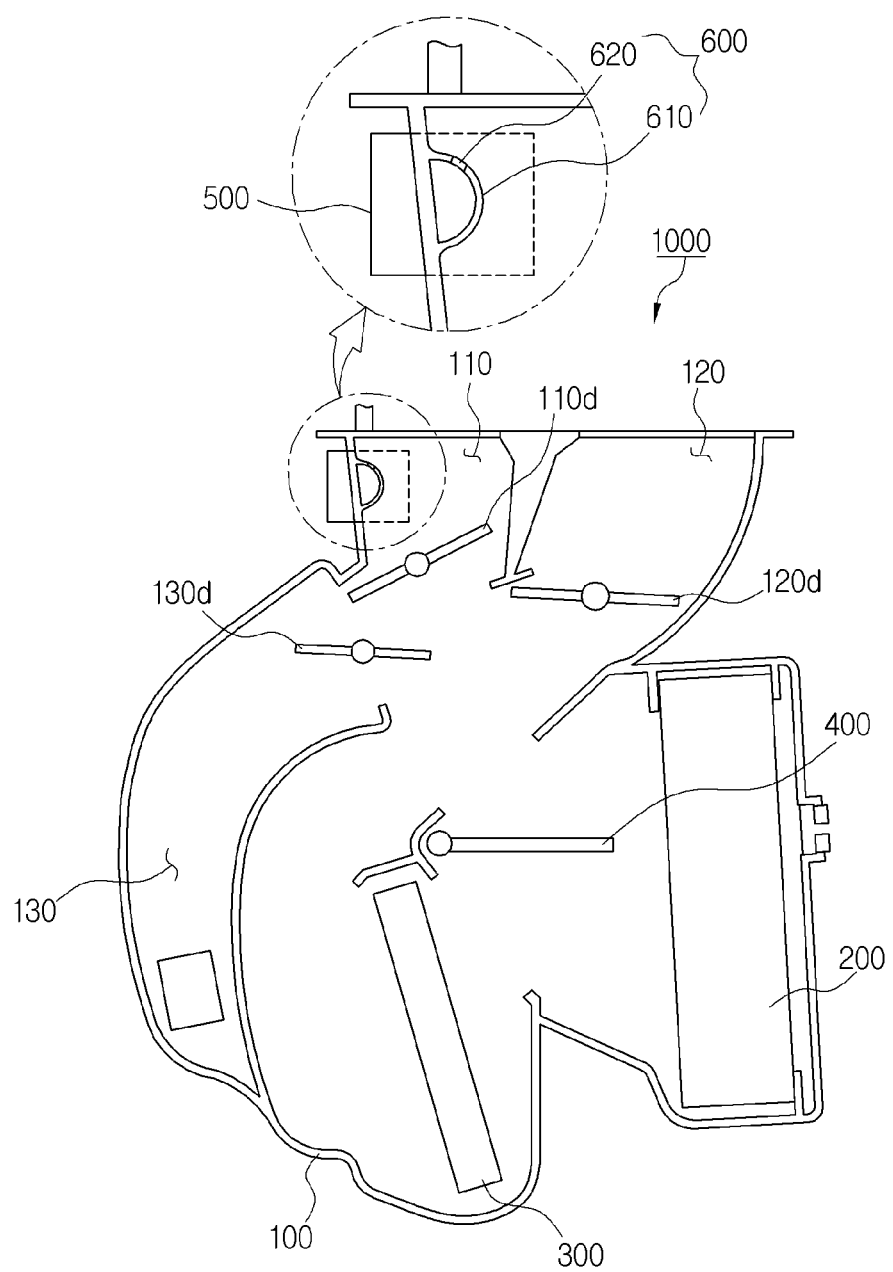
Figure 21:
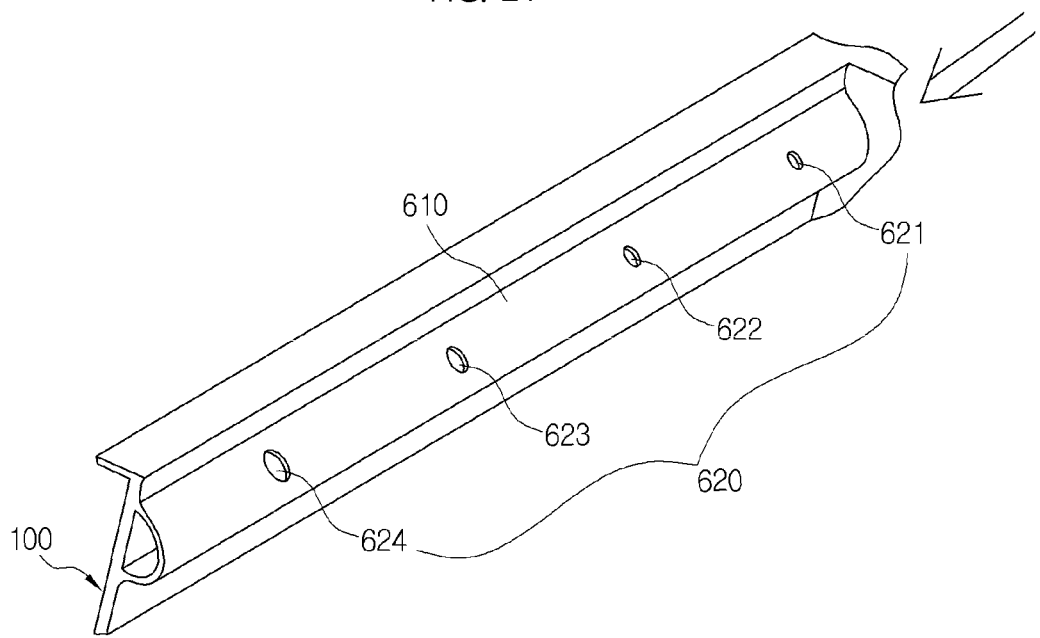
Figure 22:
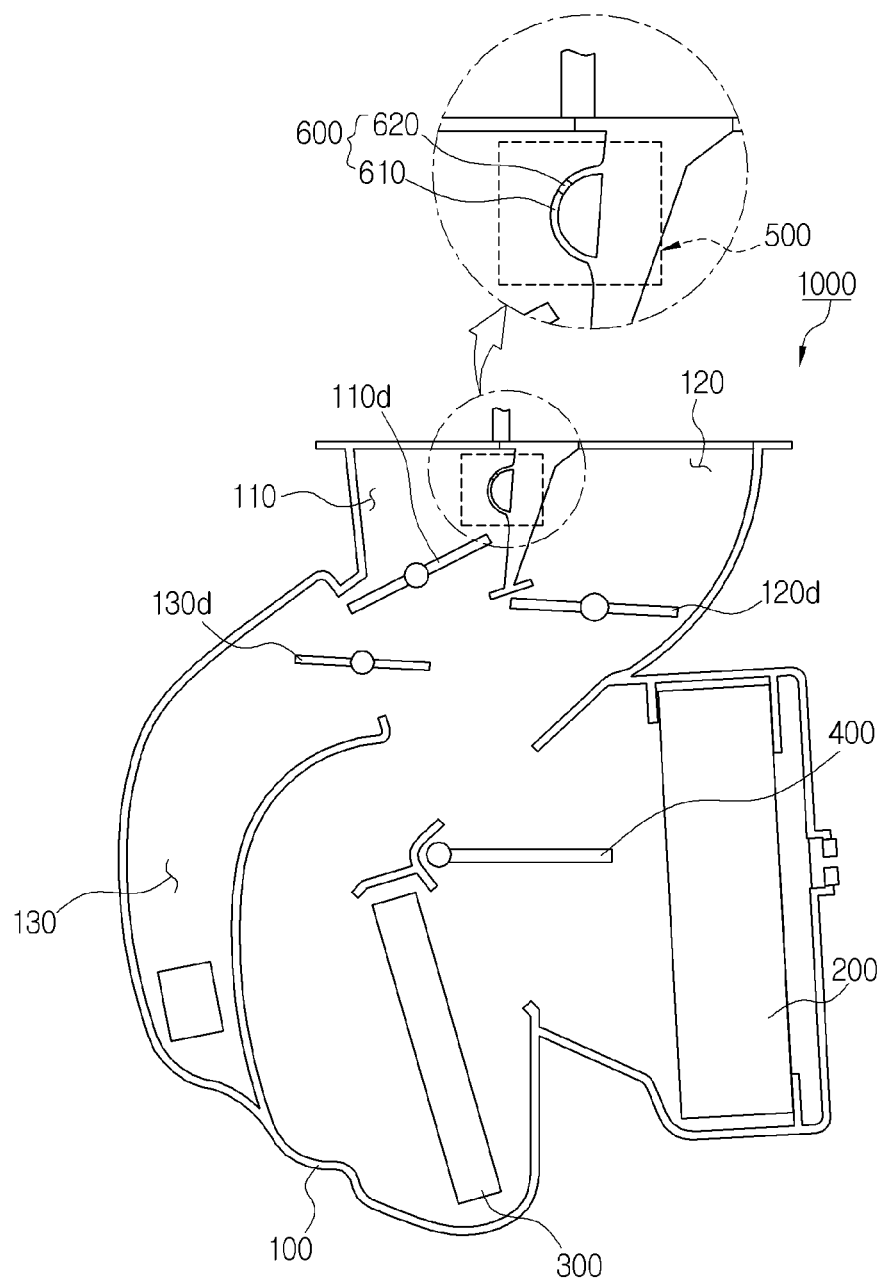
FIG. 22 is a cross-sectional view showing an air conditioner for an automobile according to still another exemplary embodiment of the present invention.

FIGS. 19 and 20 show an example in which the discharging part 600 is formed at one side wall (a left portion) forming the face vent 110, and FIG. 22 shows an example in which the discharging part 600 is formed at the other side wall (a right portion) forming the face vent 110.

The discharging part 600 is formed integrally with the inner wall surface of the air conditioning case 100, such that the air conditioner 1000 for an automobile according to the exemplary embodiment of the present invention shown in FIGS. 19 to 22 may simply obtain a perfume effect without a separate assembling process and be easily manufactured.

FIGS. 23 to 27, which are views showing still another example of the air conditioner 1000 for an automobile according to the exemplary embodiment of the present invention, show an example in which the supply pipe 700 is connected to a door axis 141 of one of the first door 110d, the second door 120d, the third door 130d, and the temp-door 400 and the door axis 141 connected to the supply pipe 700 forms the discharging part 600.

That is, the supply pipe 700 has one side connected to the air outlet 520 of the perfume generating unit 500 and the other side connected to the door axis 141 of one of the first door 110d, the second door 120d, the third door 130d, and the temp-door 400 in the air conditioning case 100 and transfers the air including the perfume component supplied from the perfume generating unit 500 to the air conditioning case 100.

In the present specification, the door axis 141 supplying the air including the perfume component among a plurality of door axes is denoted by a reference numeral 141.

Here, the other side of the supply pipe 700 is connected to the door axis 141 of one of the first door 110d, the second door 120d, the third door 130d, and the temp-door 400 in the air conditioning case 100, the door axis 141 connected to the supply pipe 700 is formed in a pipe shape in which an inner portion thereof is hollowed and is provided with one or more communication hole 620 formed in a length direction thereof by hollowing a predetermined region thereof.

That is, the air conditioner 1000 for an automobile according to the exemplary embodiment of the present invention shown in FIGS. 23 to 27 uses the door axis 141 of one of the first door 110d, the second door 120d, the third door 130d, and the temp-door 400 that are necessarily provided in the air conditioning case 100 without separately configuring the discharging part 600 for discharging the air including the perfume component.

Therefore, the air conditioner 1000 for an automobile according to the exemplary embodiment of the present invention has advantages in that the entire configuration thereof may be simplified and production efficiency thereof may be improved.

Figure 23:
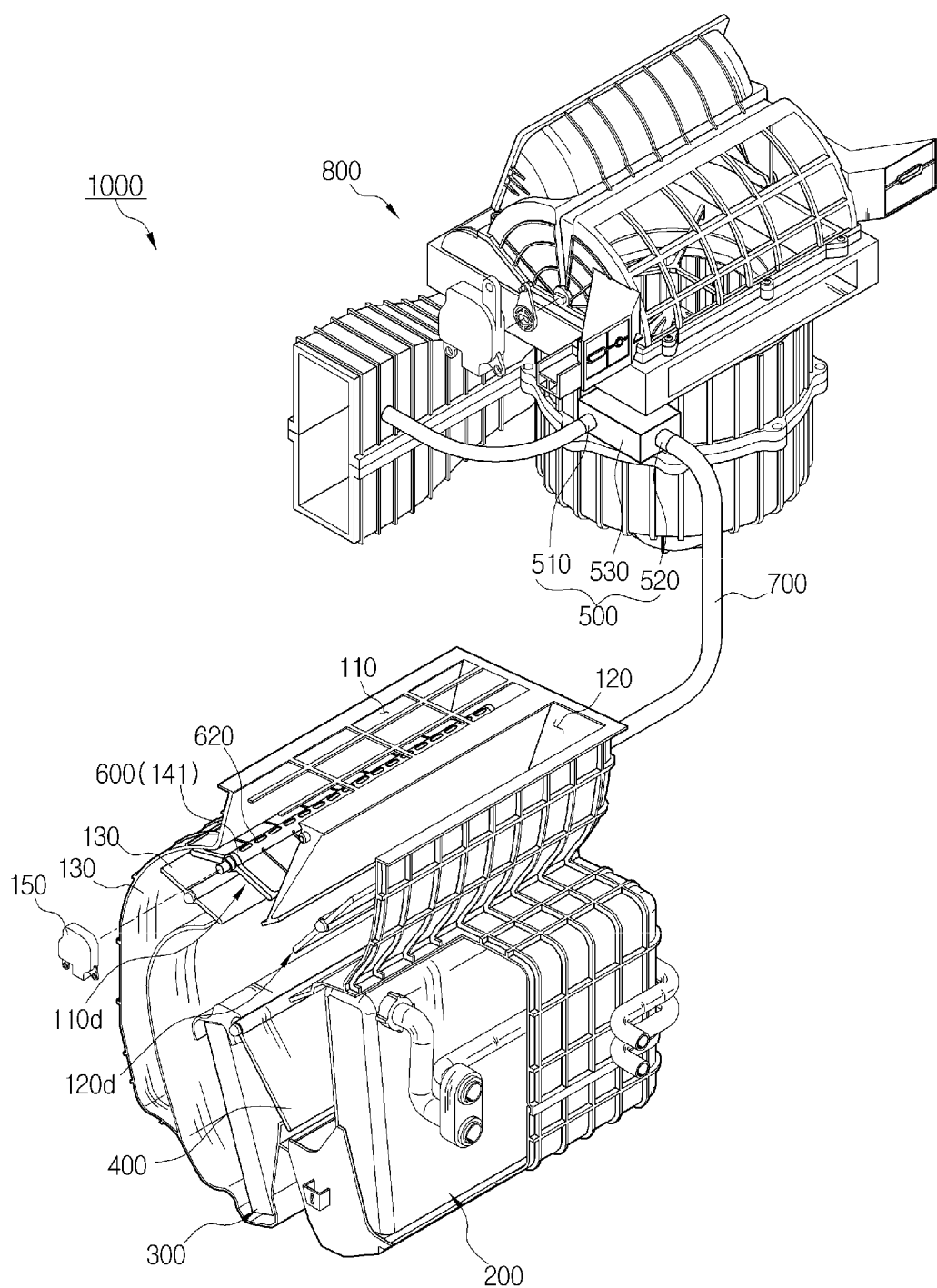
FIGS. 23 and 24 are, respectively, a perspective view and a cross-sectional view showing an air conditioner for an automobile according to still another exemplary embodiment of the present invention.

One side end portion of the first door 110d, the second door 120d, the third door 130d, and the temp-door 400 is provided with a driving unit 150 for driving the first door 110d, the second door 120d, the third door 130d, and the temp-door 400 in order to easily control a flow of the air. In FIG. 23, the driving unit 150 for driving the first door 110d is shown.

That is, the first door 110d, the second door 120d, the third door 130d, and the temp-door 400 are rotatably provided in the air conditioning case 100.

Here, the air conditioning case 100 is provided with the hollow hole 101 so that one of the first door 110d, the second door 120d, the third door 130d, and the temp-door 400 serves to easily supply the perfume component simultaneously with controlling the flow of the air and is provided with a fixing part 104 to be connected to the supply pipe 700 transferring the air including the perfume component.

Figure 26:
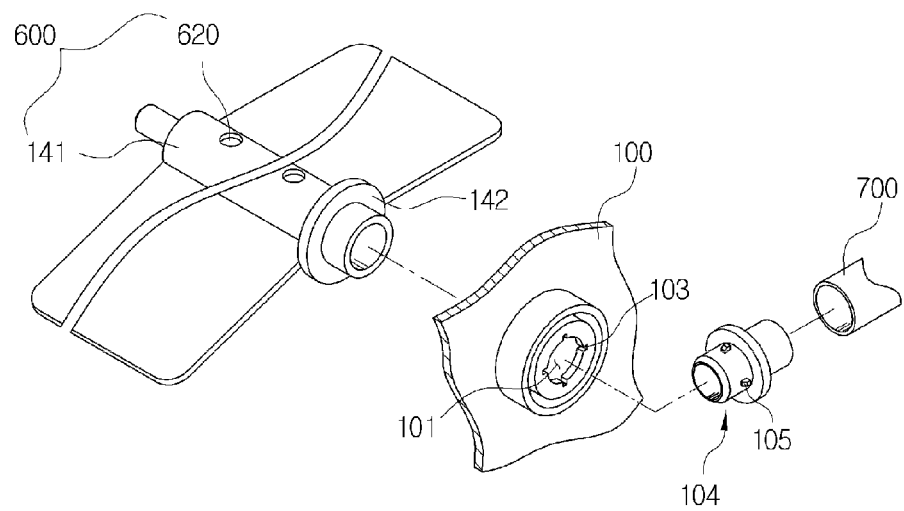
FIGS. 26 and 27 are, respectively, an exploded perspective view and a cross-sectional view showing a coupling portion of one side of a door of an air conditioner for an automobile according to the exemplary embodiment of the present invention.
Figure 27:
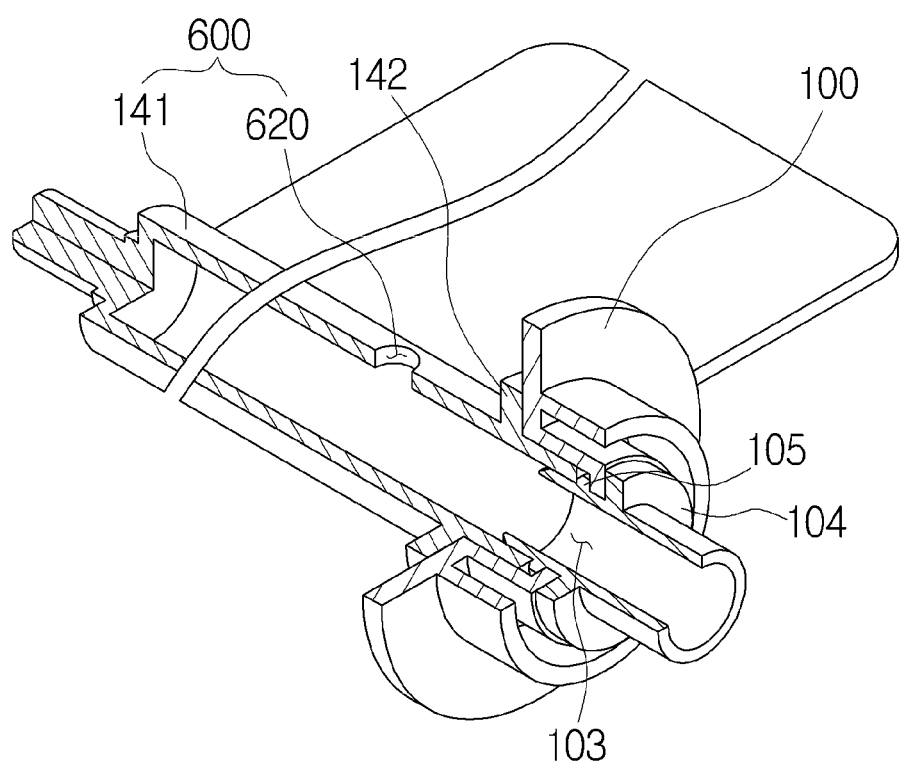

FIGS. 26 and 27 show a fixing form of the other side at which the driving axis of one of the first door 110d, the second door 120d, the third door 130d, and the temp-door 400 are not connected to the driving unit 150.

The air conditioning case 100 is provided with the hollow hole 101 formed by hollowing a predetermined region thereof and the fixing part 104 connected to the supply pipe 700 so that the air including the perfume component is transferred to the air conditioning case 100 through the hollow hole 101.

That is, the fixing part 104 is to fix the supply pipe 700 to the air conditioning case 100. In FIGS. 26 and 27, an example in which a circumference of the hollow hole 101 of the air conditioning case 100 is provided with a fastening groove 103 and the fixing part 104 is provided with a fastening protrusion 105 corresponding to the fastening groove 103 is shown.

More specifically, after the fastening protrusion 105 is inserted into the fastening groove 103, the fixing part 104 rotates by a predetermined angle, such that it is maintained in fixed state.

The fixing part 104 has a form in which an inner portion thereof is hollowed, such that it may be in communication with the hollow hole 101 or be inserted into the hollow hole 101, and is connected to the supply pipe 700.

In this configuration, the driving axis supplying the air including the perfume component is in communication with the hollow hole 101 and is rotatably provided.

In FIGS. 26 and 27, an example in which a circumferential portion of an end portion of the door axis 141 supplying the air including the perfume component is provided with a step part 141 limiting a depth at which the fixing part 104 is inserted into the door axis 141 and the end portion of the door axis 141 provided with the step part 142 is rotatably positioned between the hollow hole 101 and the fixing part 104 is shown.

Figure 24:
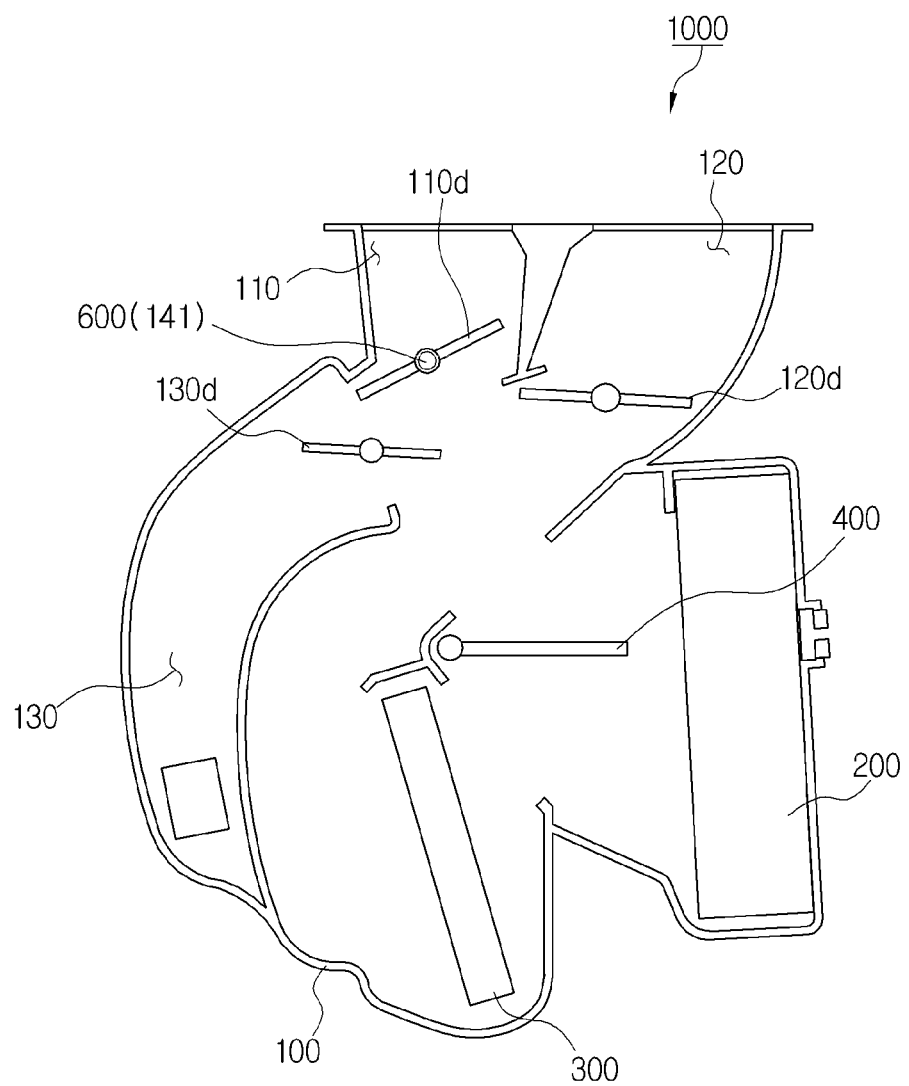
Figure 25:
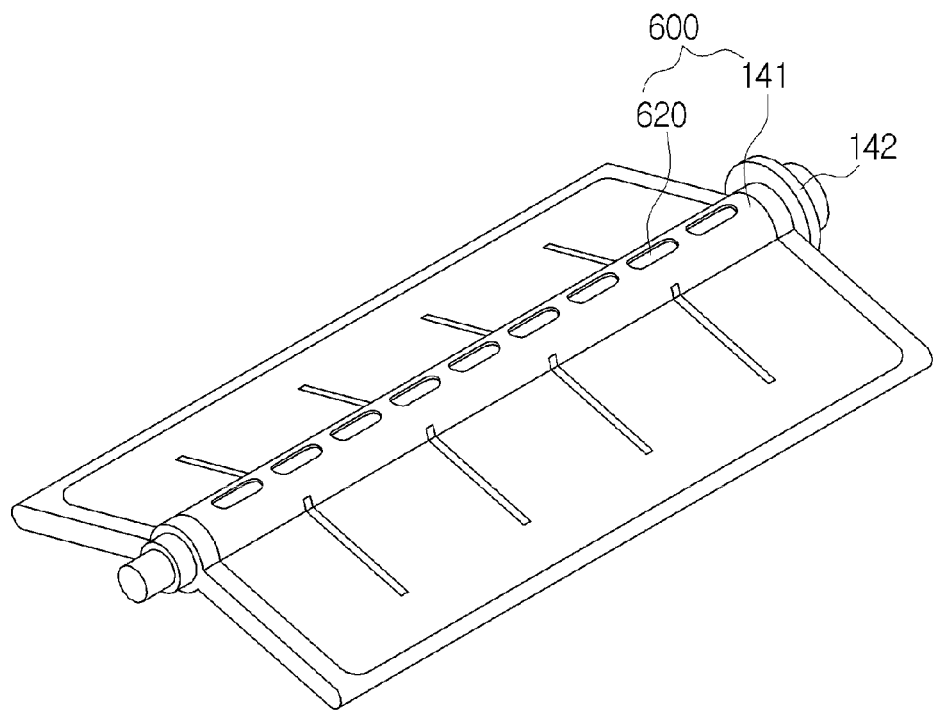
FIG. 25 is a perspective view showing a discharging part (door) of an air conditioner for an automobile according to the exemplary embodiment of the present invention.

In FIGS. 23 and 24, an example in which the door axis 141 of the first door 110d controlling the open degree of the face vent 110 in the air conditioner 1000 for an automobile according to the exemplary embodiment of the present invention forms the discharging part 600 is shown.

The air conditioner 1000 for an automobile according to the exemplary embodiment of the present invention may have various fixing schemes such as a scheme of transferring the air including the perfume component while stably supporting the door axis 141 to be rotatable.

Therefore, the air conditioner 1000 for an automobile according to the exemplary embodiment of the present invention may have uniform perfume performance in the width direction of the automobile by discharging the air mixed with the perfume component supplied from the perfume generating unit 500 into the air conditioning case using the discharging part 600 having a shape in which it is long in the length direction.

Therefore, the air conditioner for an automobile according to the present invention may have uniform perfume performance in the width direction of the automobile by discharging the air mixed with the perfume component supplied from the perfume generating unit into the air conditioning case using the discharging part having a shape in which it is long in the length direction.

Particularly, in the air conditioner for an automobile according to the exemplary embodiment of the present invention, the plurality of communication holes formed in the transferring part of the discharging part are formed to have gradually increased hollow sizes as they become distant from the air outlet of the perfume generating unit, thereby making it possible to uniformly discharge the perfume component in the width direction of the automobile regardless of the position of the perfume generating unit.

In addition, in the air conditioner for an automobile according to the exemplary embodiment of the present invention, in the case in which the transferring part of the discharging part is positioned at the region in which the mixture of the air passing through the cool air passage and the air passing through the warm air passage moves, the perfume may be uniformly supplied to the interior of the automobile through one or more of the face vent, the defrost vent, and the floor vent.

In this case, regardless of a mode determined by the passenger, the perfume component may be supplied to the interior of the automobile.

Further, in the air conditioner for an automobile according to another exemplary embodiment of the present invention, in the case in which the transferring part of the discharging part is formed to be long in the face vent, hindrance of the flow of the air by the blowing part may be minimized and the discharging of the air mixed with the perfume component to other vents may be prevented to discharge the perfume component having high concentration to the front seat side.

In this case, the air conditioner for an automobile according to the present invention may solve a problem that excessive moisture is generated in a window of the automobile due to the perfume component included in the air discharged to the defrost vent.

Furthermore, in the air conditioner for an automobile according to the present invention, at the time of inserting the discharging part from the outside of the air conditioning case into the air conditioning case and fixing the discharging part thereto, the position of the communication hole positioned in the air conditioning case may be confirmed through the indicating part of the extension part, and the hollow hole is provided with the concave part and the supporting part is provided with the concave part to prevent rotation of the discharging part, thereby making it possible to easily fix the discharging part and improve fixing force.

In addition, in the air conditioner for an automobile according to the present invention, the door axis serves as the discharging part to supply the air mixed with the perfume component without hindering the flow of the air blown by the blowing part, thereby making it possible to improve the perfume performance.

The present invention is not limited to the above-mentioned exemplary embodiments, and may be variously applied, and may be variously modified without departing from the gist of the present invention claimed in the claims.

What is claimed is:

1. An air conditioner for an automobile, comprising:
   an air conditioning case comprising a face vent having an open degree controlled by a first door, a defrost vent having an open degree controlled by a second door, a floor vent having an open degree controlled by a third door, and a hollow region;
   a blowing part connected to an inlet of the air conditioning case, the blowing part being configured to blow external air;
   an evaporator and a heater core within the air conditioning case;
   a temp-door controlling open degrees of a cool air passage and a warm air passage in the air conditioning case;
   a perfume generating unit including an air inlet through which air is introduced, an air outlet through which the air is discharged, and a perfume generating part generating a perfume;
   a discharging part connected to the air outlet of the perfume generating unit to supply the air transferred through the air outlet into the air conditioning case, wherein the discharging part includes a transferring part having a pipe shape extending in a width direction in the air conditioning case, the transferring part has a plurality of communication holes in a length direction thereof, the transferring part is integrally formed with an inner wall of the air conditioning case in such a manner that the inner wall of the air conditioning case is parallel with the length direction of the transferring part, and the discharging part is inserted within the hollow region of the air conditioning case;
   a connecting part, one side of which is connected to a side of a supply pipe so as to be connected to the air outlet of the perfume generating unit,
   a supporting part comprising a first protruded portion and a concave portion, the first protruded portion protruding from a circumference of a region between the connecting part and the transferring part and having a size capable of being inserted into the hollow region of the air conditioning case;
   a convex part comprising a second protruded portion, the second protruded portion protruding from a predetermined region of an inner circumferential surface of the hollow region of the air conditioning case toward an inner area of the hollow region of the air conditioning case, and being configured to correspond with the concave portion of the supporting part;
   an extension part formed at one side of the supporting part in an outward direction of the air conditioning case, the extension part being configured to contact an outer surface of the air conditioning case; and
   an indicating part comprising third protruded portion protruding from a predetermined region of an outer circumference of the extension part, the indicating part being indicative of a direction corresponding to a position of the communication holes in the transferring part,
   wherein a gradient of a reference direction opposing an air flow direction from the center of the discharging part in a radial direction is defined as 0 degrees, the communication holes are formed at an angle between 30 and 330 degrees from the reference direction, and the air flow direction is a direction in which air is applied to an outer side of the transferring part while the air flows inside the air conditioning case.

2. The air conditioner for an automobile of claim 1, wherein the discharging part is configured to discharge air including a perfume component in a region of the face vent, the face vent includes a driver seat side extracting part, a driver seat center extracting part, a passenger seat center extracting part, and a passenger seat side extracting part, the communication holes include a first communication hole corresponding to the driver seat side extracting part, a second communication hole corresponding to the driver seat center extracting part, a third communication hole corresponding to the passenger seat center extracting part, and a fourth communication hole corresponding to the passenger seat side extracting part, and the second and third communication holes have sizes smaller than those of the first and fourth communication holes.

3. The air conditioner for an automobile of claim 2, wherein one of the second and third communication holes, which is more distant from a supply pipe, has a size larger than that of the other, and
   one of the first and fourth communication holes, which is more distant from the supply pipe, has a size larger than that of the other.

4. The air conditioner for an automobile of claim 2, wherein the first to fourth communication holes have different sizes, respectively.

5. The air conditioner for an automobile of claim 2, wherein the driver seat side extracting part is in communication with a driver seat side channel for discharging air blown within the air conditioning case to a driver seat side,
   the driver seat center extracting part is in communication with a driver seat center channel for discharging the air blown within the air conditioning case to a driver seat center,
   the passenger seat center extracting part is in communication with a passenger seat center channel for discharging the air blown within the air conditioning case to a passenger seat center, and
   the passenger seat side extracting part is in communication with a passenger seat side channel for discharging the air blown within the air conditioning case to a passenger seat side.

6. The air conditioner for an automobile of claim 1, wherein the communication holes are formed at an angle between 90 and 270 degrees from the reference direction.

7. The air conditioner for an automobile of claim 1, wherein the communication holes are formed at an angle between 90 and 135 degrees and an angle between 225 and 270 degrees from the reference direction.

8. The air conditioner for an automobile of claim 1, wherein the discharging part is positioned at a downstream side of an air flow direction of the evaporator and the heater core.

9. The air conditioner for an automobile of claim 8, wherein the discharging part is configured to discharge air including a perfume component into a region in which a mixture of air passing through the cool air passage and air passing through the warm air passage moves.

* * * * *